United States Patent
Johnson et al.

(10) Patent No.: US 12,237,061 B2
(45) Date of Patent: Feb. 25, 2025

(54) IV WORKFLOW MANAGEMENT SYSTEM

(71) Applicant: CareFusion 303, Inc., San Diego, CA (US)

(72) Inventors: Shannon John Johnson, San Diego, CA (US); Dennis Anthony Tribble, Ormond Beach, FL (US)

(73) Assignee: CareFusion 303, Inc., San Diego, CA (US)

( * ) Notice: Subject to any disclaimer, the term of this patent is extended or adjusted under 35 U.S.C. 154(b) by 243 days.

(21) Appl. No.: 17/910,721

(22) PCT Filed: Mar. 19, 2021

(86) PCT No.: PCT/US2021/023195
§ 371 (c)(1),
(2) Date: Sep. 9, 2022

(87) PCT Pub. No.: WO2021/188921
PCT Pub. Date: Sep. 23, 2021

(65) Prior Publication Data
US 2023/0146554 A1    May 11, 2023

Related U.S. Application Data

(60) Provisional application No. 62/991,620, filed on Mar. 19, 2020.

(51) Int. Cl.
*G16H 20/13* (2018.01)
*G16H 40/67* (2018.01)

(52) U.S. Cl.
CPC ............. *G16H 20/13* (2018.01); *G16H 40/67* (2018.01)

(58) Field of Classification Search
None
See application file for complete search history.

(56) References Cited

U.S. PATENT DOCUMENTS

| | | | |
|---|---|---|---|
| 9,931,452 B2 * | 4/2018 | Pouchoulin | A61M 1/16 |
| 2013/0018356 A1 * | 1/2013 | Prince | G06Q 10/0833 |
| | | | 604/506 |
| 2013/0197927 A1 | 8/2013 | Vanderveen et al. | |

(Continued)

FOREIGN PATENT DOCUMENTS

| | | |
|---|---|---|
| CN | 109550110 A | 4/2019 |
| WO | WO-2016/118082 A1 | 7/2016 |

(Continued)

*Primary Examiner* — Brandi N Hopkins
*Assistant Examiner* — Nigel H Plumb
(74) *Attorney, Agent, or Firm* — Mintz Levin Cohn Ferris Glovsky and Popeo, P.C.

(57) ABSTRACT

A gravimetric verification system, method, and computer program product for automated detection and correction of reference density information based. An expected density of a fluid drug can be determined from the measured mass of a fluid drug and the intended volume of the fluid drug to be delivered to a medication container. The expected density can be compared to previously calculated densities for the fluid to verify the accuracy of a reference density value, verify the measurements and functional status of the measuring device for the fluid drug, and, in some instances, provide control or configuration commands to adjust one or more devices.

18 Claims, 6 Drawing Sheets

(56) References Cited

U.S. PATENT DOCUMENTS

| | | | |
|---|---|---|---|
| 2014/0135732 A1* | 5/2014 | Spronken | A61M 5/16845 |
| | | | 702/45 |
| 2016/0275441 A1* | 9/2016 | Barber | G06T 7/001 |
| 2017/0076063 A1 | 3/2017 | Louie et al. | |
| 2018/0099083 A1 | 4/2018 | Rajadhyax et al. | |
| 2018/0247703 A1* | 8/2018 | D'Amato | G16H 10/60 |
| 2019/0262231 A1* | 8/2019 | Bochenko | A61J 1/03 |

FOREIGN PATENT DOCUMENTS

| | | |
|---|---|---|
| WO | WO-2018/075079 A1 | 4/2018 |
| WO | WO-2019/244063 A1 | 12/2019 |

\* cited by examiner

IV WORKFLOW MANAGEMENT SYSTEM

CROSS-REFERENCE TO RELATED APPLICATIONS

The present application is a national stage of International Application No. PCT/US2021/023195, filed on Mar. 19, 2021, and titled, "IV Workflow Management System," which claims priority to U.S. Provisional Application No. 62/991,620, filed on Mar. 19, 2020, and titled, "Automated Specific Gravity Determination Based on Gravimetric Determinations in an IV Workflow System," the entirety of each of which is incorporated by reference herein.

FIELD

This disclosure relates generally to gravimetric verification, and more specifically to an IV workflow management system for automated density determination.

BACKGROUND

Gravimetric verification, such as used in some IV Workflow Management Software Systems (e.g., Pyxis IV Prep™), use density (e.g., a measurement of a mass of a fluid per a unit volume or measure) to compute an expected mass of a fluid to be injected into a sterile dose medication container. Gravimetric systems use this fluid mass to assess whether the correct amount of the known fluid was injected into a final medication container.

Changes in the fluid mass can also be used to determine whether or not the appropriate amount of fluid has been removed from a medication container (e.g., negative change in mass). IV workflow management systems that perform this method of gravimetric verification may retain information including a volume of a fluid intended to be delivered and a mass of the fluid actually delivered and use that information to determine whether a particular admixture was produced with acceptable accuracy.

In some instances, an IV workflow management system may use density to convert an actual change in mass back to a volume, for the purpose of proposing additional volume of drug to be added to a final dosing container to achieve accurate delivery.

For the purposes of IV workflow management systems, the necessary precision of density measurements or estimates is limited to that precision that will identify measureable changes in volume. However, there are limits to the precision of measurement that can be achieved by syringes, which are the primary tool used for such measurement, of any particular nominal volume. Healthcare providers, such as hospitals, pharmacies, and/or the like, that want to perform gravimetric verification generally (a) estimate the density of the fluid, (b) obtain density information about the fluid from individual manufacturers, (c) compute an expected density of the fluid (e.g., an expected density based on a known mass of expected active and inactive ingredients), or (d) employ laboratory determinations (e.g., a densitometer) to measure the density of the fluid, which places significant barriers around adoption of gravimetric verification, because there is no repository of such information available. Further, the range of actual fluid densities found in practice has never been studied and, therefore, given the unknown degree of variability of a given drug (e.g., same manufacturer and same lot, same manufacturer and different lot, different manufacturer, and/or the like), a "reported" density may or may not accurately reflect the density in the field. Thus, it can be difficult to verify whether there are discrepancies in the amount of fluid deposited into a dose medication container or in the amount of fluid removed from the dose medication container to be delivered to a patient. If there are discrepancies, it may also be difficult to determine when, during the IV workflow the discrepancy occurred, such as during preparation of the medication, why the discrepancy occurred, such as through user error, calibration error, labeling error, and/or the like, and/or the extent of the impact caused by the discrepancy, as the discrepancy may be aggregated across numerous healthcare providers. This inhibits quickly and efficiently correcting the discrepancy, and may result harm to the patient, such as via an incorrect dose of the fluid being delivered to the patient.

SUMMARY

Accordingly, provided are improved systems, devices, products, apparatus, and/or methods for automated density determination by an IV workflow management system (an "IVWMS"). For example, the IVWMS may determine, based on information received from a gravimetric verification system, an expected density of a fluid to be delivered to a container for comparison to a set of densities received from respective gravimetric verification systems. Based on the comparison, the IVWMS may verify the accuracy of a dose of the fluid being delivered to the container, identify trends in the dose of the fluid and/or the accuracy of the dose of the fluid, present a discrepancy in the fluid being, disable a labeling process for the container, cause one or more of the gravimetric verification systems to be recalibrated, and/or the like. Thus, the IVWMS may help to determine verify whether there are discrepancies in the amount of fluid deposited into or removed from the dose medication container, and if the IVWMS determines that a discrepancy exists, the system may determine when, during the IV workflow the discrepancy occurred, why the discrepancy occurred, the extent of the impact caused by the discrepancy, and/or the like. This may help to quickly and efficiently correct the discrepancy, or prevent the discrepancy from being repeated.

According to some non-limiting embodiments or aspects, provided is a system including: a central repository system including one or more processors programmed and/or configured to: receive, from a gravimetric verification system, an identifier for a fluid, an intended volume of a first portion of the fluid to be delivered to a medication container, and a mass of the first portion of the fluid delivered to the medication container: determine an expected density of the first portion of the fluid based on the intended volume of the first portion of the fluid and the mass of the first portion of the fluid: determine a statistical parameter of a density of the fluid based at least in part on a relationship between the expected density and a set of densities of a plurality of portions of the fluid from respective gravimetric verification systems; and based at least in part on the statistical parameter, provide the expected density of the fluid to the gravimetric verification system.

In some non-limiting embodiments or aspects, the one or more processors are further programmed and/or configured to: determine at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and store, in a data storage device, a review indicator for the expected density, said storing in response to the expected density being determined to be outside the threshold value of the previously determined expected density or the statistical parameter being determined to be outside the threshold value of the previously determined statistical parameter.

In some non-limiting embodiments or aspects, the one or more processors are further programmed and/or configured to: receive, from a second gravimetric verification system, a second intended volume of a second portion of the fluid to be delivered to a second medication container and a second mass of the second portion of the fluid delivered to the second medication container; determine a second density of the fluid based on the second intended volume and the second mass; determine the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, provide the second density of the fluid to the gravimetric verification system for updating a density value used by the gravimetric verification system for gravimetric verification of the fluid.

In some non-limiting embodiments or aspects, the one or more processors are further programmed and/or configured to: determine an amount of change in the statistical parameter of the density of the fluid over a period time; and determine, based on the determined density of the fluid and the second determined density of the of the fluid, at least one of the gravimetric verification system and the at least one second gravimetric verification system as associated with the change in the statistical parameter.

In some non-limiting embodiments or aspects, the one or more processors are further programmed and/or configured to: receive a measurement from the gravimetric verification system associated with the change in the statistical parameter; and transmit a message indicating refusal of the measurement.

In some non-limiting embodiments or aspects, the one or more processors are further programmed and/or configured to: transmit a control message to cause an adjustment of the gravimetric verification system associated with the change in the statistical parameter, wherein the adjustment includes an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

In some non-limiting embodiments or aspects, the system further includes: the gravimetric verification system, wherein the gravimetric verification system includes one or more processors programmed and/or configured to: determine a second intended volume of a portion of the fluid to be delivered to a second medication container and a second mass of the portion of the fluid delivered to the second medication container: determine a second density of the of the fluid based on the second intended volume and the second mass; and determine that the second density corresponds to the statistical parameter of the expected density of the fluid; and adjust at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

In some non-limiting embodiments or aspects, the statistical parameter includes a mean of a plurality of densities for portions of the fluid, wherein the plurality of densities includes the expected density of the first portion of the fluid.

In some non-limiting embodiments or aspects, the one or more processors are further programmed and/or configured to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

In some non-limiting embodiments or aspects, the statistical parameter includes a deviation of the expected density from a mean of a plurality of densities for portions of the fluid.

In some non-limiting embodiments or aspects, the statistical parameter includes a density likelihood indicating a degree of correspondence between the expected density for the first portion of the fluid and an aggregated density for previously generated densities for other portions of the fluid.

In some non-limiting embodiments or aspects, the one or more processors are further programmed and/or configured to: route the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

In some non-limiting embodiments or aspects, the one or more processors are further programmed and/or configured to: obtain, from a memory accessible by the central repository system, an accuracy threshold for the fluid; and determine that the statistical parameter corresponds to the accuracy threshold.

In some non-limiting embodiments or aspects, the medication container is not a syringe.

According to some non-limiting embodiments or aspects, provided is a computer-implemented method including: receiving, with at least one processor, from a gravimetric verification system, an identifier for a fluid, an intended volume of a first portion of the fluid to be delivered to a medication container, and a mass of the first portion of the fluid delivered to the medication container; determining, with at least one processor, an expected density of the first portion of the fluid based on the intended volume of the first portion of the fluid and the mass of the first portion of the fluid: determining, with at least one processor, a statistical parameter of a density of the fluid based at least in part on a relationship between the expected density and a set of densities of a plurality of portions of the fluid from respective gravimetric verification systems; and based at least in part on the statistical parameter, providing, with at least one processor, the expected density of the fluid to the gravimetric verification system.

In some non-limiting embodiments or aspects, the method further includes determining, with at least one processor, at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and storing, with at least one processor, in a data storage device, a review indicator for the expected density, said storing in response to the expected density being determined to be outside the threshold value of the previously determined expected density or the statistical parameter being determined to be outside the threshold value of the previously determined statistical parameter.

In some non-limiting embodiments or aspects, the method further includes: receiving, with at least one processor, from a second gravimetric verification system, a second intended volume of a second portion of the fluid to be delivered to a second medication container and a second mass of the second portion of the fluid delivered to the second medication container; determining, with at least one processor, a second density of the fluid based on the second intended volume and the second mass; determining, with at least one processor, the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, providing, with at least one processor, the second density of the fluid to the gravimetric verification system for updating a density value used by the gravimetric verification system for gravimetric verification of the fluid.

In some non-limiting embodiments or aspects, the method further includes: determining, with at least one processor, an amount of change in the statistical parameter of the density of the fluid over a period time; and determining, with at least one processor, based on the determined density of the fluid and the second determined density of the of the fluid, at least one of the gravimetric verification system and the at least one second gravimetric verification system as associated with the change in the statistical parameter.

In some non-limiting embodiments or aspects, the method further includes: receiving, with at least one processor, a measurement from the gravimetric verification system associated with the change in the statistical parameter; and transmitting, with at least one processor, a message indicating refusal of the measurement.

In some non-limiting embodiments or aspects, the method further includes: transmitting, with at least one processor, a control message to cause an adjustment of the gravimetric verification system associated with the change in the statistical parameter, wherein the adjustment includes an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

In some non-limiting embodiments or aspects, the method further includes: determining, with at least one processor, a second intended volume of a portion of the fluid to be delivered to a second medication container and a second mass of the portion of the fluid delivered to the second medication container; determining, with at least one processor, a second density of the of the fluid based on the second intended volume and the second mass; and determining, with at least one processor, that the second density corresponds to the statistical parameter of the expected density of the fluid; and adjusting, with at least one processor, at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

In some non-limiting embodiments or aspects, the statistical parameter includes a mean of a plurality of densities for portions of the fluid, wherein the plurality of densities includes the expected density of the first portion of the fluid.

In some non-limiting embodiments or aspects, the method further includes: obtaining, with at least one processor, from a memory accessible by the central repository system, historical means for the fluid including a first mean value for a first point in time before receipt of the intended volume of the first portion and a second mean value for a second point in time before the first point in time; detecting, with at least one processor, a density drift over time based on the historical means and the mean, wherein the drift indicates a statistically significant change over a time period spanning from the second point in time to the time the intended volume of the first portion was received; and transmitting, with at least one processor, a message indicating a change to the density for the fluid to the plurality of gravimetric verification system for use in verifying other portions of the fluid.

In some non-limiting embodiments or aspects, the statistical parameter includes a deviation of the expected density from a mean of a plurality of densities for portions of the fluid.

In some non-limiting embodiments or aspects, the statistical parameter includes a density likelihood indicating a degree of correspondence between the expected density for the first portion of the fluid and an aggregated density for previously generated densities for other portions of the fluid.

In some non-limiting embodiments or aspects, the method further includes: routing, with at least one processor, the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

In some non-limiting embodiments or aspects, the method further includes: obtaining, with at least one processor, from a memory accessible by the central repository system, an accuracy threshold for the fluid; and determining, with at least one processor, that the statistical parameter corresponds to the accuracy threshold.

In some non-limiting embodiments or aspects, the medication container is not a syringe.

According to some non-limiting embodiments or aspects, provided is a computer program product including at least one non-transitory computer-readable medium including program instructions that, when executed by at least one processor, cause the at least one processor to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical parameter of a density of the fluid based at least in part on a relationship between the expected density and a set of densities of a plurality of portions of the fluid from respective gravimetric verification systems; and based at least in part on the statistical parameter, provide the expected density of the fluid to the gravimetric verification system.

In some non-limiting embodiments or aspects, the instructions further cause the at least one processor to: determine at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and store, in a data storage device, a review indicator for the expected density, said storing in response to the expected density being determined to be outside the threshold value of the previously determined expected density or the statistical parameter being determined to be outside the threshold value of the previously determined statistical parameter.

In some non-limiting embodiments or aspects, the instructions further cause the at least one processor to: receive, from a second gravimetric verification system, a second intended volume of a second portion of the fluid to be delivered to a second medication container and a second mass of the second portion of the fluid delivered to the second medication container; determine a second density of the fluid based on the second intended volume and the second mass; determine the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, provide the second density of the fluid to the gravimetric verification system for updating a density value used by the gravimetric verification system for gravimetric verification of the fluid.

In some non-limiting embodiments or aspects, the instructions further cause the at least one processor to: determine an amount of change in the statistical parameter of the density of the fluid over a period time; and determine, based on the determined density of the fluid and the second determined density of the of the fluid, at least one of the gravimetric verification system and the at least one second gravimetric verification system as associated with the change in the statistical parameter.

In some non-limiting embodiments or aspects, the instructions further cause the at least one processor to: receive a measurement from the gravimetric verification system associated with the change in the statistical parameter; and transmit a message indicating refusal of the measurement.

In some non-limiting embodiments or aspects, the instructions further cause the at least one processor to: transmit a control message to cause an adjustment of the gravimetric verification system associated with the change in the statistical parameter, wherein the adjustment includes an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

In some non-limiting embodiments or aspects, the instructions further cause the at least one processor to: determine a second intended volume of a portion of the fluid to be delivered to a second medication container and a second mass of the portion of the fluid delivered to the second medication container; determine a second density of the of the fluid based on the second intended volume and the second mass; and determine that the second density corresponds to the statistical parameter of the expected density of the fluid; and adjust at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

In some non-limiting embodiments or aspects, the statistical parameter includes a mean of a plurality of densities for portions of the fluid, wherein the plurality of densities includes the expected density of the first portion of the fluid.

In some non-limiting embodiments or aspects, the instructions further cause the at least one processor to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

In some non-limiting embodiments or aspects, the statistical parameter includes a deviation of the expected density from a mean of a plurality of densities for portions of the fluid.

In some non-limiting embodiments or aspects, the statistical parameter includes a density likelihood indicating a degree of correspondence between the expected density for the first portion of the fluid and an aggregated density for previously generated densities for other portions of the fluid.

In some non-limiting embodiments or aspects, the instructions further cause the at least one processor to: route the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

In some non-limiting embodiments or aspects, the instructions further cause the at least one processor to: obtain, from a memory accessible by the central repository system, an accuracy threshold for the fluid; and determine that the statistical parameter corresponds to the accuracy threshold.

In some non-limiting embodiments or aspects, the medication container is not a syringe.

According to some non-limiting embodiments or aspects, provided is a system including: a central repository system including one or more processors programmed and/or configured to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical likelihood parameter of the expected density of the fluid based at least in part on a relationship between the expected density and a set of densities of a plurality of portions of the fluid from respective gravimetric verification systems; and provide the expected density of the fluid and the statistical likelihood parameter to the gravimetric verification system.

In some non-limiting embodiments or aspects, the system further includes the gravimetric verification system, wherein the gravimetric verification system includes one or more processors programmed and/or configured to: receive the expected density and the statistical likelihood parameter from the central repository system; determine that the statistical likelihood parameter corresponds to an accuracy threshold; receive a verification density for the first portion of the fluid; determine that the verification density corresponds to the expected density; and authorize the first portion of the fluid for dispensing.

In some non-limiting embodiments or aspects, the system further includes the gravimetric verification system, wherein the gravimetric verification system includes one or more processors programmed and/or configured to: route the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

In some non-limiting embodiments or aspects, the system further includes the gravimetric verification system, wherein the gravimetric verification system includes one or more processors programmed and/or configured to: determine a second intended volume of a portion of the fluid to be delivered to a second medication container and a second mass of the portion of the fluid delivered to the second medication container; determine a second expected density of the of the fluid based on the second intended volume and the second mass; and determine a second statistical likelihood parameter of the second expected density of the fluid based at least in part on a relationship between the second expected density and the set of densities of a plurality of portions of the fluid from the respective gravimetric verification systems; and provide the second expected density of the fluid and the second statistical likelihood parameter to the gravimetric verification system.

In some non-limiting embodiments or aspects, the statistical likelihood parameter includes a density likelihood parameter indicating a degree of correspondence between the expected density for the first portion of the fluid and an aggregated density for previously generated densities for other portions of the fluid.

In some non-limiting embodiments or aspects, the one or more processors are further programmed and/or configured to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

According to some non-limiting embodiments or aspects, provided is a computer-implemented method including: receiving, with at least one processor, from a gravimetric verification system, an identifier for a fluid, an intended volume of a first portion of the fluid to be delivered to a medication container, and a mass of the first portion of the fluid delivered to the medication container; determining, with at least one processor, an expected density of the first portion of the fluid based on the intended volume of the first portion of the fluid and the mass of the first portion of the fluid; determining, with at least one processor, a statistical likelihood parameter of the expected density of the fluid based at least in part on a relationship between the expected density and a set of densities of a plurality of portions of the fluid from respective gravimetric verification systems; and providing, with at least one processor, the expected density of the fluid and the statistical likelihood parameter to the gravimetric verification system.

In some non-limiting embodiments or aspects, the method further includes: receiving, with at least one processor, the expected density and the statistical likelihood parameter from the central repository system; determining, with at least one processor that the statistical likelihood parameter corresponds to an accuracy threshold; receiving, with at least one processor, a verification density for the first portion of the fluid; determining, with at least one processor, that the verification density corresponds to the expected density; and authorizing, with at least one processor, the first portion of the fluid for dispensing.

In some non-limiting embodiments or aspects, the method further includes: routing, with at least one processor, the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

In some non-limiting embodiments or aspects, the method further includes: determining, with at least one processor, a second intended volume of a portion of the fluid to be delivered to a second medication container and a second mass of the portion of the fluid delivered to the second medication container; determining, with at least one processor, a second expected density of the of the fluid based on the second intended volume and the second mass; and determining, with at least one processor, a second statistical likelihood parameter of the second expected density of the fluid based at least in part on a relationship between the second expected density and the set of densities of a plurality of portions of the fluid from the respective gravimetric verification systems; and providing, with at least one processor, the second expected density of the fluid and the second statistical likelihood parameter to the gravimetric verification system.

In some non-limiting embodiments or aspects, the statistical likelihood parameter includes a density likelihood parameter indicating a degree of correspondence between the expected density for the first portion of the fluid and an aggregated density for previously generated densities for other portions of the fluid.

In some non-limiting embodiments or aspects, the method further includes: obtaining, with at least one processor, from a memory accessible by the central repository system, historical means for the fluid including a first mean value for a first point in time before receipt of the intended volume of the first portion and a second mean value for a second point in time before the first point in time; detecting, with at least one processor, a density drift over time based on the historical means and the mean, wherein the drift indicates a statistically significant change over a time period spanning from the second point in time to the time the intended volume of the first portion was received; and transmitting, with at least one processor, a message indicating a change to the density for the fluid to the plurality of gravimetric verification system for use in verifying other portions of the fluid.

According to some non-limiting embodiments or aspects, provided is a computer program product including at least one non-transitory computer-readable medium including program instructions that, when executed by at least one processor, cause the at least one processor to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical likelihood parameter of the expected density of the fluid based at least in part on a relationship between the expected density and a set of densities of a plurality of portions of the fluid from respective gravimetric verification systems; and provide the expected density of the fluid and the statistical likelihood parameter to the gravimetric verification system.

In some non-limiting embodiments or aspects, the instructions further cause the at least one processor to: receive the expected density and the statistical likelihood parameter from the central repository system; determine that the statistical likelihood parameter corresponds to an accuracy threshold; receive a verification density for the first portion of the fluid; determine that the verification density corresponds to the expected density; and authorize the first portion of the fluid for dispensing.

In some non-limiting embodiments or aspects, the instructions further cause the at least one processor to: route the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

In some non-limiting embodiments or aspects, the instructions further cause the at least one processor to: determine a second intended volume of a portion of the fluid to be delivered to a second medication container and a second mass of the portion of the fluid delivered to the second medication container; determine a second expected density of the of the fluid based on the second intended volume and the second mass; and determine a second statistical likelihood parameter of the second expected density of the fluid based at least in part on a relationship between the second expected density and the set of densities of a plurality of portions of the fluid from the respective gravimetric verification systems; and provide the second expected density of the fluid and the second statistical likelihood parameter to the gravimetric verification system.

In some non-limiting embodiments or aspects, the statistical likelihood parameter includes a density likelihood parameter indicating a degree of correspondence between the expected density for the first portion of the fluid and an aggregated density for previously generated densities for other portions of the fluid.

In some non-limiting embodiments or aspects, the instructions further cause the at least one processor to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

Further embodiments or aspects are set forth in the following numbered clauses:

Clause 1. A system comprising: a central repository system including one or more processors programmed and/or configured to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical parameter of a density of the fluid based at least in part on a relationship between the expected density and a set of densities of a plurality of portions of the fluid from respective gravimetric verification systems; and based at least in part on the statistical parameter, provide the expected density of the fluid to the gravimetric verification system.

Clause 2. The system of clause 1, wherein the one or more processors are further programmed and/or configured to: determine at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and store, in a data storage device, a review indicator for the expected density, said storing in response to the expected density being determined to be outside the threshold value of the previously determined expected density or the statistical parameter being determined to be outside the threshold value of the previously determined statistical parameter.

Clause 3. The system of any of clauses 1 and 2, wherein the one or more processors are further programmed and/or configured to: receive, from a second gravimetric verification system, a second intended volume of a second portion of the fluid to be delivered to a second medication container and a second mass of the second portion of the fluid delivered to the second medication container; determine a second density of the fluid based on the second intended volume and the second mass; determine the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, provide the second density of the fluid to the gravimetric verification system for updating a density value used by the gravimetric verification system for gravimetric verification of the fluid.

Clause 4. The system of any of clauses 1-3, wherein the one or more processors are further programmed and/or configured to: determine an amount of change in the statistical parameter of the density of the fluid over a period time; and determine, based on the determined density of the fluid and the second determined density of the of the fluid, at least one of the gravimetric verification system and the at least one second gravimetric verification system as associated with the change in the statistical parameter.

Clause 5. The system of any of clauses 1-4, wherein the one or more processors are further programmed and/or configured to: receive a measurement from the gravimetric verification system associated with the change in the statistical parameter; and transmit a message indicating refusal of the measurement.

Clause 6. The system of any of clauses 1-5, wherein the one or more processors are further programmed and/or configured to: transmit a control message to cause an adjustment of the gravimetric verification system associated with the change in the statistical parameter, wherein the adjustment comprises an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

Clause 7. The system of any of clauses 1-6, further comprising: the gravimetric verification system, wherein the gravimetric verification system includes one or more processors programmed and/or configured to: determine a second intended volume of a portion of the fluid to be delivered to a second medication container and a second mass of the portion of the fluid delivered to the second medication container; determine a second density of the of the fluid based on the second intended volume and the second mass; and determine that the second density corresponds to the statistical parameter of the expected density of the fluid; and adjust at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

Clause 8. The system of any of clauses 1-7, wherein the statistical parameter includes a mean of a plurality of densities for portions of the fluid, wherein the plurality of densities includes the expected density of the first portion of the fluid.

Clause 9. The system of any of clauses 1-8, wherein the one or more processors are further programmed and/or configured to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

Clause 10. The system of any of clauses 1-9, wherein the statistical parameter includes a deviation of the expected density from a mean of a plurality of densities for portions of the fluid.

Clause 11. The system of any of clauses 1-10, wherein the statistical parameter includes a density likelihood indicating a degree of correspondence between the expected density for the first portion of the fluid and an aggregated density for previously generated densities for other portions of the fluid.

Clause 12. The system of any of clauses 1-11, wherein the one or more processors are further programmed and/or configured to: route the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

Clause 13. The system of any of clauses 1-12, wherein the one or more processors are further programmed and/or configured to: obtain, from a memory accessible by the central repository system, an accuracy threshold for the fluid; and determine that the statistical parameter corresponds to the accuracy threshold.

Clause 14. The system of any of clauses 1-13, wherein the medication container is not a syringe.

Clause 15. A computer-implemented method comprising: receiving, with at least one processor, from a gravimetric verification system, an identifier for a fluid, an intended volume of a first portion of the fluid to be delivered to a medication container, and a mass of the first portion of the fluid delivered to the medication container; determining, with at least one processor, an expected density of the first portion of the fluid based on the intended volume of the first portion of the fluid and the mass of the first portion of the fluid; determining, with at least one processor, a statistical parameter of a density of the fluid based at least in part on a relationship between the expected density and a set of densities of a plurality of portions of the fluid from respective gravimetric verification systems; and based at least in part on the statistical parameter, providing, with at least one processor, the expected density of the fluid to the gravimetric verification system.

Clause 16. The computer-implemented method of clause 15, further comprising: determining, with at least one processor, at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and storing, with at least one processor, in a data storage device, a review indicator for the expected density, said storing in response to the expected density being determined to be outside the threshold value of the previously determined expected density or the statistical parameter being determined to be outside the threshold value of the previously determined statistical parameter.

Clause 17. The computer-implemented method of any of clauses 15 and 16, further comprising: receiving, with at least one processor, from a second gravimetric verification system, a second intended volume of a second portion of the fluid to be delivered to a second medication container and a second mass of the second portion of the fluid delivered to the second medication container; determining, with at least one processor, a second density of the fluid based on the second intended volume and the second mass; determining, with at least one processor, the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, providing, with at least one processor, the second density of the fluid to the gravimetric verification system for updating a density value used by the gravimetric verification system for gravimetric verification of the fluid.

Clause 18. The computer-implemented method of any of clauses 15-17, further comprising: determining, with at least one processor, an amount of change in the statistical parameter of the density of the fluid over a period time; and determining, with at least one processor, based on the determined density of the fluid and the second determined density of the of the fluid, at least one of the gravimetric verification system and the at least one second gravimetric verification system as associated with the change in the statistical parameter.

Clause 19. The computer-implemented method of any of clauses 15-18, further comprising: receiving, with at least one processor, a measurement from the gravimetric verification system associated with the change in the statistical parameter; and transmitting, with at least one processor, a message indicating refusal of the measurement.

Clause 20. The computer-implemented method of any of clauses 15-19, further comprising: transmitting, with at least one processor, a control message to cause an adjustment of the gravimetric verification system associated with the change in the statistical parameter, wherein the adjustment comprises an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

Clause 21. The computer-implemented method of any of clauses 15-20, further comprising: determining, with at least one processor, a second intended volume of a portion of the fluid to be delivered to a second medication container and a second mass of the portion of the fluid delivered to the second medication container; determining, with at least one processor, a second density of the of the fluid based on the second intended volume and the second mass; and determining, with at least one processor, that the second density corresponds to the statistical parameter of the expected density of the fluid; and adjusting, with at least one processor, at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

Clause 22. The computer-implemented method of any of clauses 15-21, wherein the statistical parameter includes a mean of a plurality of densities for portions of the fluid, wherein the plurality of densities includes the expected density of the first portion of the fluid.

Clause 23. The computer-implemented method of any of clauses 15-22, further comprising: obtaining, with at least one processor, from a memory accessible by the central repository system, historical means for the fluid including a first mean value for a first point in time before receipt of the intended volume of the first portion and a second mean value for a second point in time before the first point in time; detecting, with at least one processor, a density drift over time based on the historical means and the mean, wherein the drift indicates a statistically significant change over a time period spanning from the second point in time to the time the intended volume of the first portion was received; and transmitting, with at least one processor, a message indicating a change to the density for the fluid to the plurality of gravimetric verification system for use in verifying other portions of the fluid.

Clause 24. The computer-implemented method of any of clauses 15-23, wherein the statistical parameter includes a deviation of the expected density from a mean of a plurality of densities for portions of the fluid.

Clause 25. The computer-implemented method of any of clauses 15-24, wherein the statistical parameter includes a density likelihood indicating a degree of correspondence between the expected density for the first portion of the fluid and an aggregated density for previously generated densities for other portions of the fluid.

Clause 26. The computer-implemented method of any of clauses 15-25, further comprising: routing, with at least one processor, the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

Clause 27. The computer-implemented method of any of clauses 15-26, further comprising: obtaining, with at least one processor, from a memory accessible by the central repository system, an accuracy threshold for the fluid; and determining, with at least one processor, that the statistical parameter corresponds to the accuracy threshold.

Clause 28. The computer-implemented method of any of clauses 15-27, wherein the medication container is not a syringe.

Clause 29. A computer program product comprising at least one non-transitory computer-readable medium including program instructions that, when executed by at least one processor, cause the at least one processor to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical parameter of a density of the fluid based at least in part on a relationship between the expected density and a set of densities of a plurality of portions of the fluid from respective gravimetric verification systems; and based at least in part on the statistical parameter, provide the expected density of the fluid to the gravimetric verification system.

Clause 30. The computer program product of clause 29, wherein the instructions further cause the at least one processor to: determine at least one of (i) whether the expected density corresponds to a first threshold range or value of a previously determined expected density for the fluid and (ii) whether the statistical parameter is corresponds to a second threshold range or value compared to a previously determined statistical parameter to warrant at least one of: a modification to the existing density value or a publication of the expected density to the plurality of gravimetric verification systems; and store, in a data storage device, a review indicator for the expected density, said storing in response to the expected density being determined to be outside the threshold value of the previously determined expected density or the statistical parameter being determined to be outside the threshold value of the previously determined statistical parameter.

Clause 31. The computer program product of any of clauses 29 and 30, wherein the instructions further cause the at least one processor to: receive, from a second gravimetric verification system, a second intended volume of a second portion of the fluid to be delivered to a second medication container and a second mass of the second portion of the fluid delivered to the second medication container; determine a second density of the fluid based on the second intended volume and the second mass; determine the statistical parameter of the density of the fluid based at least in part on a relationship between the second density and the set of densities of the plurality of portions of the fluid from respective gravimetric verification systems, wherein the set of densities includes the expected density for the first portion of the fluid; and based at least in part on the statistical parameter, provide the second density of the fluid to the gravimetric verification system for updating a density value used by the gravimetric verification system for gravimetric verification of the fluid.

Clause 32. The computer program product of any of clauses 29-31, wherein the instructions further cause the at least one processor to: determine an amount of change in the statistical parameter of the density of the fluid over a period time; and determine, based on the determined density of the fluid and the second determined density of the of the fluid, at least one of the gravimetric verification system and the at least one second gravimetric verification system as associated with the change in the statistical parameter.

Clause 33. The computer program product of any of clauses 29-32, wherein the instructions further cause the at least one processor to: receive a measurement from the gravimetric verification system associated with the change in the statistical parameter; and transmit a message indicating refusal of the measurement.

Clause 34. The computer program product of any of clauses 29-33, wherein the instructions further cause the at least one processor to: transmit a control message to cause an adjustment of the gravimetric verification system associated with the change in the statistical parameter, wherein the adjustment comprises an adjustment to at least one of: a display, a power state of the gravimetric verification system associated with the change in the statistical parameter, an operational status of the gravimetric verification system associated with the change in the statistical parameter, a configuration value used by the gravimetric verification system associated with the change in the statistical parameter, or any combination thereof.

Clause 35. The computer program product of any of clauses 29-34, wherein the instructions further cause the at least one processor to: determine a second intended volume of a portion of the fluid to be delivered to a second medication container and a second mass of the portion of the fluid delivered to the second medication container; determine a second density of the of the fluid based on the second intended volume and the second mass; and determine that the second density corresponds to the statistical parameter of the expected density of the fluid; and adjust at least one element of the gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

Clause 36. The computer program product of any of clauses 29-35, wherein the statistical parameter includes a mean of a plurality of densities for portions of the fluid, wherein the plurality of densities includes the expected density of the first portion of the fluid.

Clause 37. The computer program product of any of clauses 29-36, wherein the instructions further cause the at least one processor to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

Clause 38. The computer program product of any of clauses 29-37, wherein the statistical parameter includes a deviation of the expected density from a mean of a plurality of densities for portions of the fluid.

Clause 39. The computer program product of any of clauses 29-38, wherein the statistical parameter includes a density likelihood indicating a degree of correspondence between the expected density for the first portion of the fluid and an aggregated density for previously generated densities for other portions of the fluid.

Clause 40. The computer program product of any of clauses 29-39, wherein the instructions further cause the at least one processor to: route the expected density to a processing path of a plurality of processing paths, the routing based on the degree of correspondence, wherein the plurality of processing paths includes: for a first degree of correspondence, generating a mean statistical density for the fluid including the expected density for the first portion of the fluid; for a second degree of correspondence, filtering the expected density from consideration for the fluid; and for a third degree of correspondence, transmitting the expected density for presentation and review via a graphical user interface.

Clause 41. The computer program product of any of clauses 29-40, wherein the instructions further cause the at least one processor to: obtain, from a memory accessible by the central repository system, an accuracy threshold for the fluid; and determine that the statistical parameter corresponds to the accuracy threshold.

Clause 42. The computer program product of any of clauses 29-41, wherein the medication container is not a syringe.

Clause 43. A system comprising: a central repository system including one or more processors programmed and/or configured to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical likelihood parameter of the expected density of the fluid based at least in part on a relationship between the expected density and a set of densities of a plurality of portions of the fluid from respective gravimetric verification systems; and provide the expected density of the fluid and the statistical likelihood parameter to the gravimetric verification system.

Clause 44. The system of clause 43, further comprising the gravimetric verification system, wherein the gravimetric verification system includes one or more processors programmed and/or configured to: receive the expected density and the statistical likelihood parameter from the central repository system; determine that the statistical likelihood parameter corresponds to an accuracy threshold; receive a verification density for the first portion of the fluid; determine that the verification density corresponds to the expected density; and authorize the first portion of the fluid for dispensing.

Clause 45. The system of any of clauses 43 and 44, further comprising the gravimetric verification system, wherein the gravimetric verification system includes one or more processors programmed and/or configured to: route the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

Clause 46. The system of any of clauses 43-45, further comprising the gravimetric verification system, wherein the gravimetric verification system includes one or more processors programmed and/or configured to: determine a second intended volume of a portion of the fluid to be delivered to a second medication container and a second mass of the portion of the fluid delivered to the second medication container; determine a second expected density of the of the fluid based on the second intended volume and the second mass; and determine a second statistical likelihood parameter of the second expected density of the fluid based at least in part on a relationship between the second expected density and the set of densities of a plurality of portions of the fluid from the respective gravimetric verification systems; and provide the second expected density of the fluid and the second statistical likelihood parameter to the gravimetric verification system.

Clause 47. The system of any of clauses 43-46, wherein the statistical likelihood parameter includes a density likelihood parameter indicating a degree of correspondence between the expected density for the first portion of the fluid and an aggregated density for previously generated densities for other portions of the fluid.

Clause 48. The system of any of clauses 43-47, wherein the one or more processors are further programmed and/or configured to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

Clause 49. A computer-implemented method comprising: receiving, with at least one processor, from a gravimetric verification system, an identifier for a fluid, an intended volume of a first portion of the fluid to be delivered to a medication container, and a mass of the first portion of the fluid delivered to the medication container; determining, with at least one processor, an expected density of the first portion of the fluid based on the intended volume of the first portion of the fluid and the mass of the first portion of the fluid; determining, with at least one processor, a statistical likelihood parameter of the expected density of the fluid based at least in part on a relationship between the expected density and a set of densities of a plurality of portions of the fluid from respective gravimetric verification systems; and providing, with at least one processor, the expected density of the fluid and the statistical likelihood parameter to the gravimetric verification system.

Clause 50. The computer-implemented method of clause 49, further comprising: receiving, with at least one processor, the expected density and the statistical likelihood parameter from the central repository system; determining, with at least one processor that the statistical likelihood parameter corresponds to an accuracy threshold; receiving, with at least one processor, a verification density for the first portion of the fluid; determining, with at least one processor, that the verification density corresponds to the expected density; and authorizing, with at least one processor, the first portion of the fluid for dispensing.

Clause 51. The computer-implemented method of any of clauses 49 and 50, further comprising: routing, with at least one processor, the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

Clause 52. The computer-implemented method of any of clauses 49-51, further comprising: determining, with at least one processor, a second intended volume of a portion of the fluid to be delivered to a second medication container and a second mass of the portion of the fluid delivered to the second medication container; determining, with at least one processor, a second expected density of the of the fluid based on the second intended volume and the second mass; and determining, with at least one processor, a second statistical likelihood parameter of the second expected density of the fluid based at least in part on a relationship between the second expected density and the set of densities of a plurality of portions of the fluid from the respective gravimetric verification systems; and providing, with at least one processor, the second expected density of the fluid and the second statistical likelihood parameter to the gravimetric verification system.

Clause 53. The computer-implemented method of any of clauses 49-52, wherein the statistical likelihood parameter includes a density likelihood parameter indicating a degree of correspondence between the expected density for the first portion of the fluid and an aggregated density for previously generated densities for other portions of the fluid.

Clause 54. The computer-implemented method of any of clauses 49-53, further comprising: obtaining, with at least one processor, from a memory accessible by the central repository system, historical means for the fluid including a first mean value for a first point in time before receipt of the intended volume of the first portion and a second mean value for a second point in time before the first point in time; detecting, with at least one processor, a density drift over time based on the historical means and the mean, wherein the drift indicates a statistically significant change over a time period spanning from the second point in time to the time the intended volume of the first portion was received; and transmitting, with at least one processor, a message indicating a change to the density for the fluid to the plurality of gravimetric verification system for use in verifying other portions of the fluid.

Clause 55. A computer program product comprising at least one non-transitory computer-readable medium including program instructions that, when executed by at least one processor, cause the at least one processor to: receive, from a gravimetric verification system, an identifier for a fluid, an intended volume of a first portion of the fluid to be delivered to a medication container, and a mass of the first portion of the fluid delivered to the medication container; determine an expected density of the first portion of the fluid based on the intended volume of the first portion of the fluid and the mass of the first portion of the fluid; determine a statistical likelihood parameter of the expected density of the fluid based at least in part on a relationship between the expected density and a set of densities of a plurality of portions of the fluid from respective gravimetric verification systems; and provide the expected density of the fluid and the statistical likelihood parameter to the gravimetric verification system.

Clause 56. The computer program product of clause 55, wherein the instructions further cause the at least one processor to: receive the expected density and the statistical likelihood parameter from the central repository system; determine that the statistical likelihood parameter corresponds to an accuracy threshold; receive a verification density for the first portion of the fluid; determine that the verification density corresponds to the expected density; and authorize the first portion of the fluid for dispensing.

Clause 57. The computer program product of any of clauses 55 and 56, wherein the instructions further cause the at least one processor to: route the expected density to a processing path of a plurality of processing paths, the routing based on the statistical likelihood parameter, wherein the plurality of processing paths includes: authorizing the first portion of the fluid for dispensing; transmitting a request to review the first portion of the fluid; and adjusting at least one of: a display, a power state of the gravimetric verification system, an operational status of the gravimetric verification system, or a configuration value used by the gravimetric verification system.

Clause 58. The computer program product of any of clauses 55-57, wherein the instructions further cause the at least one processor to: determine a second intended volume of a portion of the fluid to be delivered to a second medication container and a second mass of the portion of the fluid delivered to the second medication container; determine a second expected density of the of the fluid based on the second intended volume and the second mass; and determine a second statistical likelihood parameter of the second expected density of the fluid based at least in part on a relationship between the second expected density and the set of densities of a plurality of portions of the fluid from the respective gravimetric verification systems; and provide the second expected density of the fluid and the second statistical likelihood parameter to the gravimetric verification system.

Clause 59. The computer program product of any of clauses 55-58, wherein the statistical likelihood parameter includes a density likelihood parameter indicating a degree of correspondence between the expected density for the first portion of the fluid and an aggregated density for previously generated densities for other portions of the fluid.

Clause 60. The computer program product of any of clauses 55-59, wherein the instructions further cause the at least one processor to: obtain, from a memory accessible by the central repository system, historical means for the fluid including a first mean value for a first point in time before receipt of the intended volume of the first portion and a second mean value for a second point in time before the first point in time; detect a density drift over time based on the historical means and the mean, wherein the drift indicates a statistically significant change over a time period spanning from the second point in time to the time the intended volume of the first portion was received; and transmit a message indicating a change to the density for the fluid to the plurality of gravimetric verification system for use in verifying other portions of the fluid.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of limits. As used in the specification and the claims, the singular form of "a," "an," and "the" include plural referents unless the context clearly dictates otherwise.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein.

Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

BRIEF DESCRIPTION OF THE DRAWINGS

Additional advantages and details are explained in greater detail below with reference to the exemplary embodiments or aspects that are illustrated in the accompanying schematic figures, in which.

DETAILED DESCRIPTION

Figure 1:
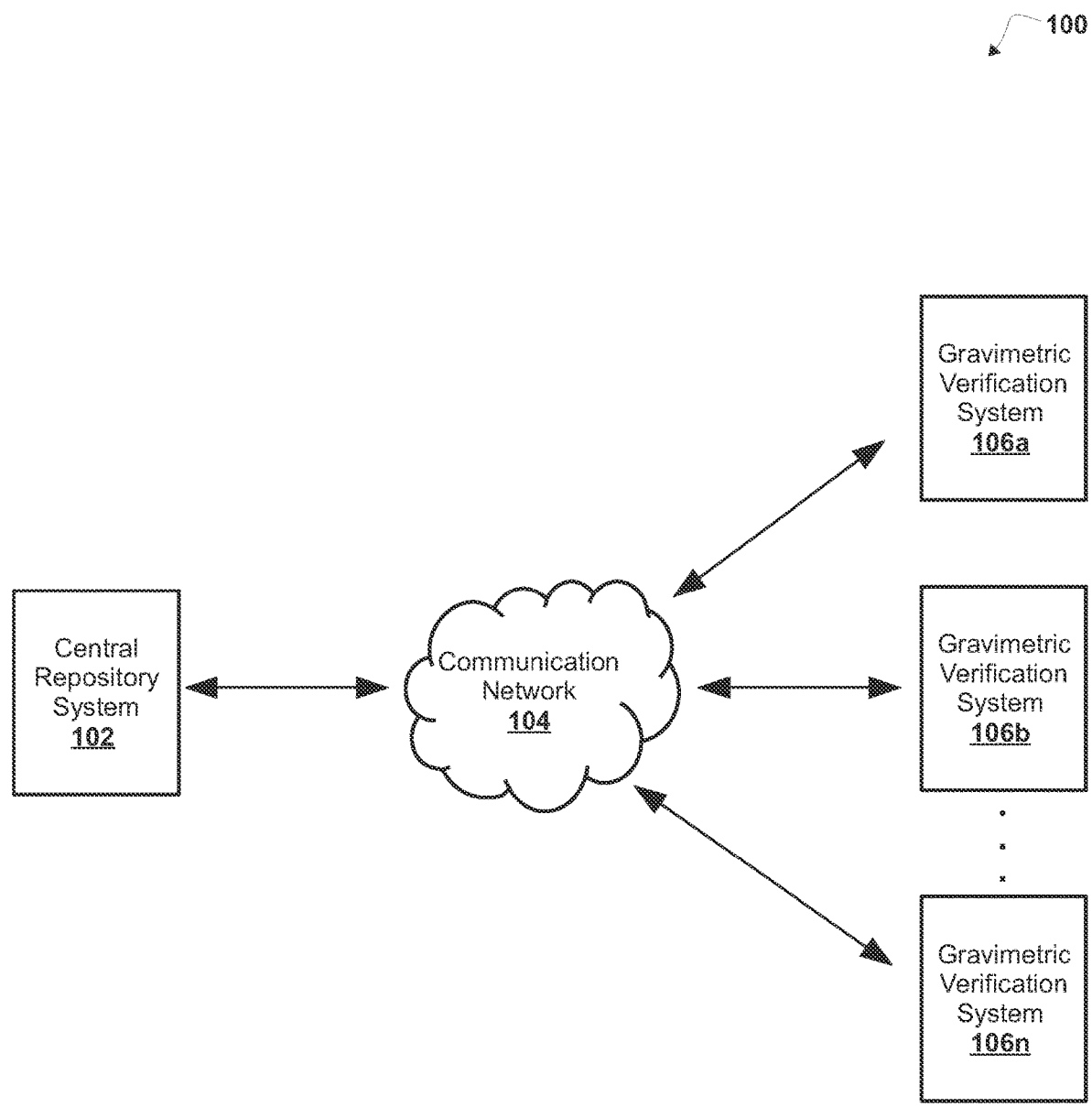
FIG. 1 is a diagram of non-limiting embodiments or aspects of an IV workflow management system including an environment in which systems, devices, products, apparatus, and/or methods, described herein, may be implemented.

It is to be understood that the present disclosure may assume various alternative variations and step sequences, except where expressly specified to the contrary. It is also to be understood that the specific devices and processes illustrated in the attached drawings, and described in the following specification, are simply exemplary and non-limiting embodiments or aspects. Hence, specific dimensions and other physical characteristics related to the embodiments or aspects disclosed herein are not to be considered as limiting.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having." or the like are intended to be open-ended terms. Further, the phrase "based on" is intended to mean "based at least partially on" unless explicitly stated otherwise.

As used herein, the terms "communication" and "communicate" refer to the receipt or transfer of one or more signals, messages, commands, or other type of data. For one unit (e.g., any device, system, or component thereof) to be in communication with another unit means that the one unit is able to directly or indirectly receive data from and/or transmit data to the other unit. This may refer to a direct or indirect connection that is wired and/or wireless in nature. Additionally, two units may be in communication with each other even though the data transmitted may be modified, processed, relayed, and/or routed between the first and second unit. For example, a first unit may be in communication with a second unit even though the first unit passively receives data and does not actively transmit data to the second unit. As another example, a first unit may be in communication with a second unit if an intermediary unit processes data from one unit and transmits processed data to the second unit. It will be appreciated that numerous other arrangements are possible.

It will be apparent that systems and/or methods, described herein, can be implemented in different forms of hardware, software, or a combination of hardware and software. The actual specialized control hardware or software code used to implement these systems and/or methods is not limiting of the implementations. Thus, the operation and behavior of the systems and/or methods are described herein without reference to specific software code, it being understood that software and hardware can be designed to implement the systems and/or methods based on the description herein.

Some non-limiting embodiments or aspects are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, etc.

For purposes of the description hereinafter, the terms "end," "upper," "lower," "right," "left," "vertical," "horizontal," "top," "bottom," "lateral," "longitudinal," and derivatives thereof shall relate to non-limiting embodiments or aspects as they are oriented in the drawing figures. However, it is to be understood that non-limiting embodiments or aspects may assume various alternative variations and step sequences, except where expressly specified to the contrary. It is also to be understood that the specific devices and processes illustrated in the attached drawings, and described in the following specification, are simply exemplary embodiments or aspects. Hence, specific dimensions and other physical characteristics related to the embodiments or aspects of the embodiments or aspects disclosed herein are not to be considered as limiting unless otherwise indicated.

As used herein, the term "computing device" or "computer device" may refer to one or more electronic devices that are configured to directly or indirectly communicate with or over one or more networks. The computing device may be a mobile device, a desktop computer, or the like. Furthermore, the term "computer" may refer to any computing device that includes the necessary components to receive, process, and output data, and normally includes a display, a processor, a memory, an input device, and a network interface. An "application" or "application program interface" (API) refers to computer code or other data sorted on a computer-readable medium that may be executed by a processor to facilitate the interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, touchscreen, etc.).

As used herein, the term "server" may refer to or include one or more processors or computers, storage devices, or similar computer arrangements that are operated by or facilitate communication and processing for multiple parties in a network environment, such as the Internet, although it will be appreciated that communication may be facilitated over one or more public or private network environments and that various other arrangements are possible. Further, multiple computers, e.g., servers, or other computerized devices, such as POS devices, directly or indirectly communicating in the network environment may constitute a "system," such as a merchant's POS system.

Provided is an improved IVWMS for automated density determination.

Gravimetric verification, such as used in some IVWMSs, use density (e.g., a measurement of a mass of a fluid per a unit volume or measure) to compute an expected mass of a fluid to be injected into a sterile dose medication container. Gravimetric systems use this fluid mass to assess whether the correct amount of the known fluid was injected into a final medication container. In some instances, the term "specific gravity" is used in place of the term "density." Note that a specific gravity is a ratio of substance density to a standard substance (typically water). As a ratio, it has no units of measure and cannot be used to compute mass or volume. In such instances, the term "specific gravity" is used as an imprecise synonym for the term "density." An expected change in mass of a fluid may be defined according to the following Equation (1):

$$\text{expected change in mass} = \text{expected volume (mL)} \times \text{density}\left(\frac{g}{mL}\right) \quad (1)$$

In some instances, an IVWMS may use density to convert an actual change in mass back to a volume, for the purpose of proposing additional volume of drug to be added to a final dosing container to achieve accurate delivery. An actual volume of a fluid delivered may be defined according to the following Equation (2):

$$\text{actual volume delivered} = \text{change in mass} \frac{(g)}{\text{density}\left(\frac{g}{mL}\right)} \quad (2)$$

An additional delivered volume of a fluid may be defined according to the following Equation (3):

$$\text{additional delivered volume} = \text{expected volume} - \text{actual volume delivered} \quad (3)$$

For the purposes of IVWMS, the necessary precision of density measurements or estimates is limited to that precision that will identify measureable changes in volume. For example, as described in at least ISO 7886-1, there are limits to the precision of measurement that can be achieved by a syringe of any particular nominal volume. So, variances in density that would result in immeasurable differences in volume provide no meaningful value. For example, specifying density to the nearest mg per mL of fluid, produces no value, because, in no case could any known syringe measure the resulting difference in volume computed by application of that difference in density.

As used herein, a "fluid" generally refers to a mixture that contains a specific drug or mixture of drugs that may be further diluted (with a specified diluent) to a specific concentration.

IVWMS's may use an electronic balance to determine a change in mass associated with a delivery of an ingredient or drug into a final dose medication container. As noted above, the vast majority of such deliveries are accurate within the limits of accuracy associated with a device, such as a syringe, used to deliver the dose to the medication container. While some measurements captured may be erroneous, the capture and analysis of large numbers of doses statistically eliminates outliers, and the same statistics may expose variations in density observed in the field. Densities can differ based on a variety of factors such as variances in manufacturing, changes in manufacturer's formulation, or an environmental condition at the time of measurement (e.g., the temperature or elevation relative to sea level). Such variations can impact powdered injections whose fill quantity in a vial can be substantially higher than the labeled quantity. The impact of such differences can be minor but may have unknown or unintended impacts. For example, children or elderly recipients having low body mass may have an unanticipated response to minor differences in an amount of a substance administered.

It is further worth mentioning that such variations are only significant to the extent that they can predict measurable differences between intended and actual volume. Furthermore, the medication container may include a syringe, bottle, vial, bag, or other container for receiving a medication or diluent therefor. The medication container may be a container which will be delivered for administration to the patient or may be a container used as an intermediate receptacle during preparation of a fluid. In some implementations, negative verification may be performed whereby analysis is performed to confirm the volume, mass, or density of a fluid removed from a medication container. For example, a stock bottle may have a volume of a fluid removed for preparing a single dose for a patient. In such an example, the stock bottle may be the medication container analyzed.

The IVWMS consistent with implementations of the current subject matter can detect when the density may be inaccurate and affect a change in the verification system to address the inaccuracy. An expected density of a fluid drug can be determined from the measured mass (of a fluid drug) and the intended volume of the fluid drug to be delivered to a medication container. The following Equation (4) defines one expression of how an expected density may be generated:

$$\text{density} = \frac{\text{change in mass (g)}}{\text{expected change in volume (mL)}} \quad (4)$$

The expected density can be compared to a sample of previously calculated expected densities to generate a parameter estimating the likelihood that the old value is a) outside a threshold range and b) statistically and significantly different than the existing value. When this happens, the fluid drug density value may be flagged for review so that the existing density value being used in the gravimetric verification system might be updated to a more accurate value.

Features may be implemented in a system, method, or computer program product that includes an IVMS for automated density determination from a gravimetric verification system. The density determination may be based on receipt of reported deliveries of an intended volume of a specific fluid to be delivered to a medication container and the measured change in mass of the receiving medication container after such delivery to determine an estimated density of the specified fluid. The determination may be based on a relationship between the change in mass and an expected change in volume, such as that defined by Equation (4) defined herein above.

The automated determination may include comparing this density to a mean density generated from previously received reports regarding the specified fluid and determining whether or not this measurement is likely to be sufficiently accurate for inclusion in a new determination of a mean density for the specified fluid (e.g., whether or not this measurement satisfies a threshold difference between this density and the mean density, etc.). The determined density may be used in combination with previously received computed densities to generate a new mean density for this fluid. The new mean density may be compared to the previously-derived mean density for the specified fluid, and a determination of whether or not the addition of the new density makes unacceptable changes in the computed mean density (indicating a likely error in measurement) is performed. The features may include providing the statistical parameter of the density of the fluid to the gravimetric verification system for verifying an expected density value and (in certain configurations) updating a density value used in the gravimetric verification system for gravimetric verification of other instances of the fluid.

Non-limiting embodiments or aspects of the present disclosure are directed to systems, methods, and computer program products for automated density determination that receive, from a gravimetric verification system, an intended volume of a fluid to be delivered to a medication container and a mass of the fluid delivered to the medication container; determine a density of the fluid based on the intended volume of the fluid and the mass of the fluid; determine a statistical parameter of the density of the fluid based on the determined density of the fluid and a previously determined statistical parameter of the density of the fluid; and provide the statistical parameter of the density of the fluid to the gravimetric verification system for updating a density value used in the gravimetric verification system for gravimetric verification.

In this way, an agreed upon density for a particular drug at a particular concentration in a particular diluent, which is determined from an organically changing data library updated based on measurements from many different gravimetric verification systems, may be provided for updating a density value used in the gravimetric verification systems for gravimetric verification. Accordingly, predicated on the notion that the vast majority of such measurements are very nearly accurate (within the limits of capability of a device used to perform the measurement), non-limiting embodiments or aspects of the current subject matter statistically analyze such densities over a large number of measurements and statistically determine what the actual density of any given injection or delivery would be based on experience in the field. Using the large number of doses of any particular drug accrued from healthcare provider usage, a statistical model of the density that can be used to determine a range of densities experienced in the field for any particular concentration of any particular drug is generated and provided.

The IVWMS may determine, based on information received from a gravimetric verification system, an expected density of a fluid to be delivered to a container for comparison to a set of densities received from respective gravimetric verification systems. Based on the comparison, the IVWMS consistent with implementations of the current subject matter may verify the accuracy of a dose of the fluid being delivered to the container, identify trends in the dose of the fluid and/or the accuracy of the dose of the fluid, present a discrepancy in the fluid being, disable a labeling process for the container, cause one or more of the gravimetric verification systems to be recalibrated, and/or the like. Thus, the IVWMS may help to determine verify whether there are discrepancies in the amount of fluid deposited into or removed from the dose medication container, and if the IVWMS determines that a discrepancy exists, the system may determine when, during the IV workflow the discrepancy occurred, why the discrepancy occurred, the extent of the impact caused by the discrepancy, and/or the like. This may help to quickly and efficiently correct the discrepancy, or prevent the discrepancy from being repeated.

Referring now to FIG. 1, FIG. 1 is a diagram of the IVMS 100 including an example environment in which devices, systems, methods, and/or products described herein, may be implemented. As shown in FIG. 1, IVMS 100 includes central repository system 102, communication network 104, and one or more gravimetric verification systems 106 (e.g., a first gravimetric verification system 106a, a second gravimetric verification system 106b, an nth gravimetric verification system 106n, etc.). Central repository system 104 and the one or more gravimetric verification systems 106 may interconnect (e.g., establish a connection to communicate, etc.) via wired connections, wireless connections, or a combination of wired and wireless connections.

Central repository system 102 may include one or more devices capable of receiving information and/or data from the one or more gravimetric verification systems 106 (e.g., via communication network 104, etc.) and/or communicating information and/or data to the one or more gravimetric verification systems 106 (e.g., via communication network 104, etc.). For example, central repository system 102 may include a computing device, such as a server, a group of servers, and/or other like devices. In some non-limiting embodiments or aspects, central repository system 102 may include and/or access one or more one or more internal and/or external databases including volume data, mass data, density data, statistical parameter data, fluid data, drug concentration data, diluent concentration data, and/or the like.

A gravimetric verification system 106 may include one or more devices capable of receiving information and/or data from other gravimetric verification systems 106 and/or central repository system 102 (e.g., via communication network 104, etc.) and/or communicating information and/or data to the other gravimetric verification systems 106 and/or central repository system 102 (e.g., via communication network 104, etc.). For example, central repository system 102 may include a computing device, such as a server, a group of servers, and/or other like devices. In some non-limiting embodiments or aspects, gravimetric verification system 102 may include a pharmacy compounding system or IV workflow system configured to deliver or inject fluid to a medication container and perform gravimetric verification of the fluid delivered or injected into the medication container, such as the Pyxis IV Prep™, and/or the like.

Communication network 104 may include one or more wired and/or wireless networks. For example, communication network 104 may include a cellular network (e.g., a long-term evolution (LTE) network, a third generation (3G) network, a fourth generation (4G) network, a fifth generation (5G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network, an ad hoc network, an intranet, the Internet, a fiber optic-based network, a cloud computing network, and/or the like, and/or a combination of these or other types of networks.

The number and arrangement of devices and systems shown in FIG. 1 is provided as an example. There may be additional devices and/or systems, fewer devices and/or systems, different devices and/or systems, or differently arranged devices and/or systems than those shown in FIG. 1. Furthermore, two or more devices and/or systems shown in FIG. 1 may be implemented within a single device and/or system, or a single device and/or system shown in FIG. 1 may be implemented as multiple, distributed devices and/or systems. Additionally, or alternatively, a set of devices and/or systems (e.g., one or more devices or systems) of IVWMS 100 may perform one or more functions described as being performed by another set of devices or systems of IVWMS 100.

Figure 2:
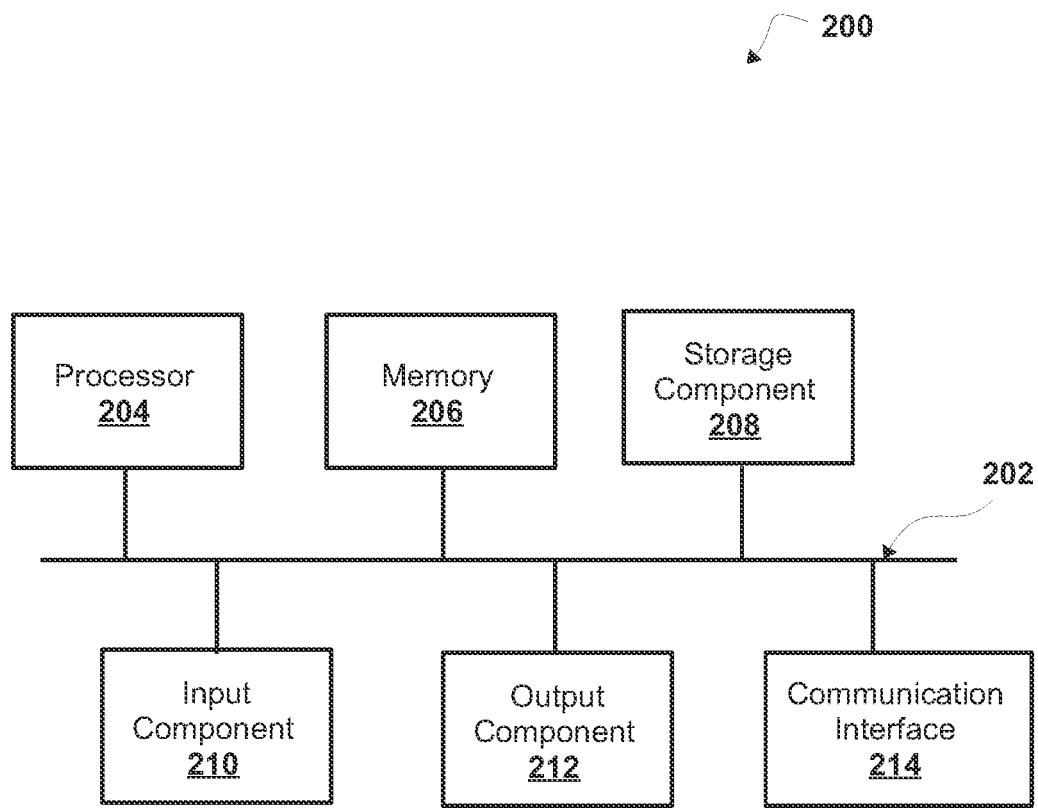
FIG. 2 is a block diagram of non-limiting embodiments or aspects of components of a computing system including one or more devices and/or one or more systems of FIG. 1.

Referring now to FIG. 2, FIG. 2 is a diagram of example components of a device 200. Device 200 may correspond to one or more devices of transaction processing network 101, one or more devices of merchant system 102, one or more devices of payment gateway system 104, one or more devices of acquirer system 106, one or more devices of transaction service provider system 108, one or more devices of issuer system 110, user device 112 (e.g., one or more devices of a system of user device 112, etc.), and/or one or more devices of communication network 114. In some non-limiting embodiments or aspects, one or more devices of transaction processing network 101, one or more devices of merchant system 102, one or more devices of payment gateway system 104, one or more devices of acquirer system 106, one or more devices of transaction service provider system 108, one or more devices of issuer system 110, user device 112 (e.g., one or more devices of a system of user device 112, etc.), and/or one or more devices of communication network 114 can include at least one device 200 and/or at least one component of device 200. As shown in FIG. 2, device 200 may include a bus 202, a processor 204, memory 206, a storage component 208, an input component 210, an output component 212, and a communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.) that can be programmed to perform a function. Memory 206 may include random access memory (RAM), read only memory (ROM), and/or another type of dynamic or static storage device (e.g., flash memory, magnetic memory, optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210) may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmitter, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi® interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

Memory 206 and/or storage component 208 may include data storage or one or more data structures (e.g., a database, etc.). Device 200 may be capable of receiving information from, storing information in, communicating information to, or searching information stored in the data storage or one or more data structures in memory 206 and/or storage component 208.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3:
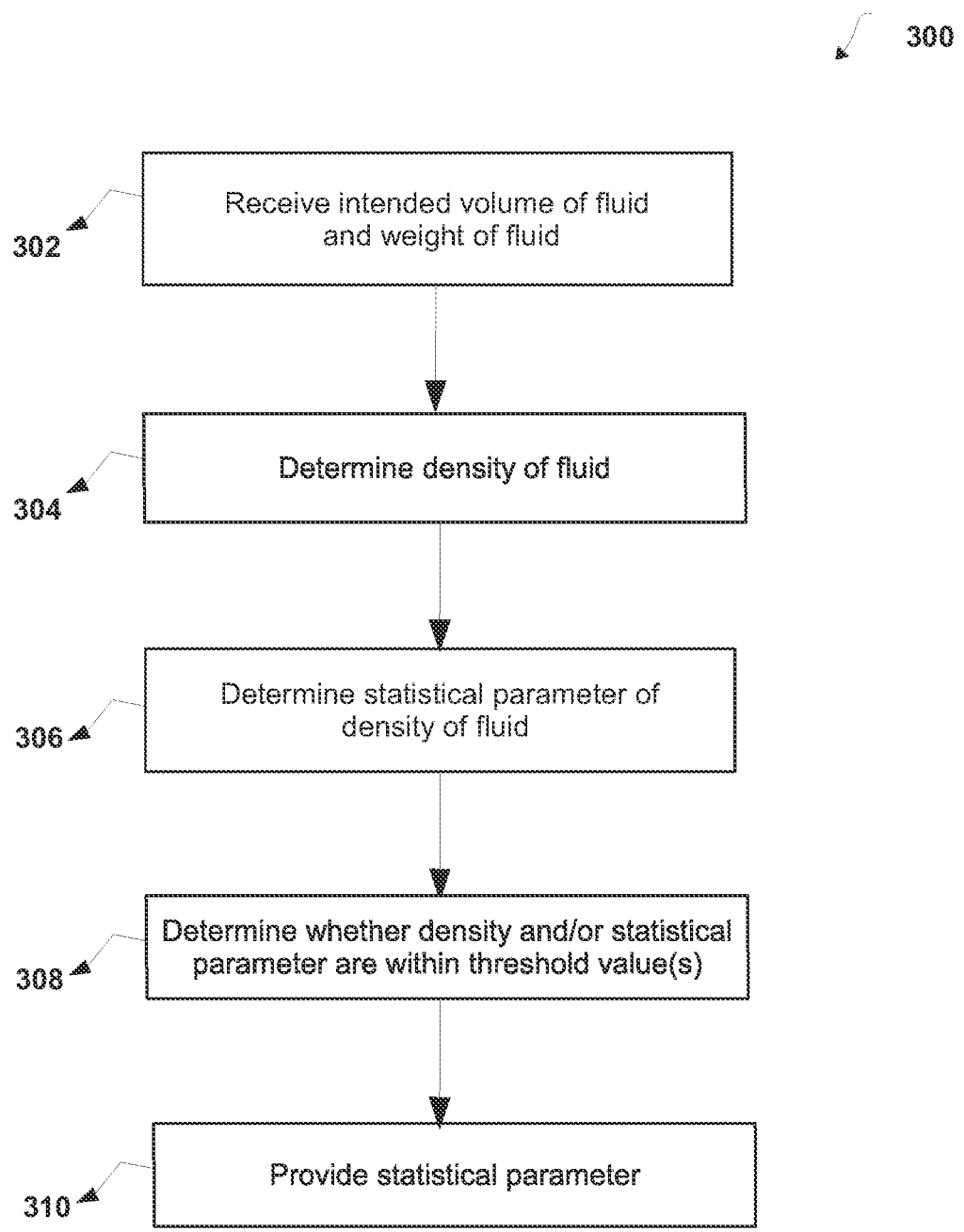
FIG. 3 is a flowchart of a non-limiting embodiment or aspect of a process for automated density determination.

Referring now to FIG. 3, FIG. 3 is a flowchart of non-limiting embodiments or aspects of a process 300 for automated density determination. In some non-limiting embodiments or aspects, one or more of the steps of process 300 may be performed (e.g., completely, partially, etc.) by central repository system 102 (e.g., one or more devices of central repository system 102, etc.). In some non-limiting embodiments or aspects, one or more of the steps of process 300 may be performed (e.g., completely, partially, etc.) by another device or a group of devices separate from or including central repository system 106, such as the one or more gravimetric verification systems 106 (e.g., one or more devices of the one or more gravimetric verification systems 106, etc.).

As shown in FIG. 3, at step 302, process 300 includes receiving an intended volume of a fluid to be delivered to a medication container and a mass of the fluid delivered to the medication container. For example, central repository system 102 may receive, from gravimetric verification system 106a, an intended volume of a fluid to be delivered to a medication container and a mass of the fluid delivered to the medication container. In some non-limiting embodiments or aspects, central repository system 102 may receive, from a plurality of different gravimetric verification systems 106a, 106b, ... 106n, an intended volume of a plurality of different fluids to be delivered to a plurality of different medication containers and a mass of the plurality of different fluids delivered to the plurality of different medication containers.

In some non-limiting embodiments or aspects, in order to prepare gravimetric verification system 106a to deliver a fluid to a medication container, the gravimetric verification system 106a may receive a selection, such as a user selection of a dose of the fluid (e.g., a medication, etc.) to prepare and scan information or data associated with the ingredients for the fluid into gravimetric verification system 106a. If preparation of the fluid uses reconstitution of one or more ingredients, the user may draw a diluent for reconstitution and reconstitute the ingredients with the diluent as the fluid (e.g., a drug/diluent combination, etc.) in a temporary container. Gravimetric verification system 106a may determine whether a volume of the fluid is within a tolerance threshold and, if the volume is within the tolerance threshold, draw the dose of the fluid for delivery to a medication container. Otherwise, if preparation of the medication does not involve reconstitution, the user may draw the dose of the fluid (e.g., a drug/diluent and/or solute combination, etc.) for delivery to the medication container. Gravimetric verification system 106a may tare-weigh the medication container before delivery of the fluid into the medication container and, after delivery of the fluid into the medication container, weigh the medication container including the fluid. Gravimetric verification system 106a may determine whether an amount of change between the empty medication container and the medication container filled with the fluid is within a threshold tolerance and, if the amount of change is within the threshold tolerance, record the intended volume (e.g., in mL, etc.) of the fluid that was intended to be delivered to the medication container and the mass (e.g., in gm, etc.) of the fluid actually delivered to the medication container (e.g., a difference between the mass of the empty medication container and the mass of the medication container after delivery of the fluid thereto, etc.). For example, since density is a function of the concentration of the drug and the concentration of the carrier fluid in which it is solubilized, gravimetric verification system 106a may receive or determine the following information for a dose of a fluid; an ingredient/drug type (e.g., drug type data, etc.), a concentration of the ingredient/drug (e.g., drug concentration data, etc.), a diluent used to prepare the ingredient/drug (e.g., diluent type data, etc.), a concentration of the diluent (e.g., diluent concentration data), an intended volume of the fluid to be delivered (e.g., volume data, etc.), a change in mass of the medication container to which the fluid is delivered (e.g., mass data, etc.), or any combination thereof. In such an example, since syringes used to measure fluids have known dead space that can significantly affect the mass determination of a syringe, doses may be prepared in bottles or bags for which the dead space of the syringe is not a factor.

Gravimetric verification system 106a may communicate the intended volume of the fluid to be delivered to the medication container and the mass of the fluid delivered to the medication container to central repository system 102, and central repository system 102 may translate the received information or data to global reference values (e.g., drug and diluent to global reference values, etc.).

As shown in FIG. 3, at step 304, process 300 includes determining a density of a fluid based on an intended volume of a fluid to be delivered and a mass of the fluid delivered. For example, central repository system 102 may determine a density of the fluid based on the intended volume of the fluid to be delivered and the mass of the fluid delivered. As an example, central repository system 102 may determine the density of the fluid as the mass of the fluid delivered to the medication container divided by the intended volume of the fluid that was to be delivered to the medication container. In some non-limiting embodiments or aspects, central repository system 102 may determine a density of a plurality of different fluids based on the intended volume of each fluid to be delivered and the mass of that fluid delivered.

As shown in FIG. 3, at step 306, process 300 includes determining a statistical parameter of a density of a fluid based on a determined density of the fluid and a previously determined statistical parameter of the density of the fluid. For example, central repository system 102 may determine a statistical parameter (e.g., a mean, etc.) of the density of the fluid based on the determined density of the fluid and a previously determined statistical parameter of the density of the fluid. As an example, central repository system 102 may determine and store as at least one previously determined statistical parameter a previously determined density for a particular fluid (e.g., for a particular drug at a particular concentration, etc.) based on measurements from many different gravimetric verification systems 106a. 106b . . . 106n, etc. from statistically analyzing such densities over a large number of measurements to determine an actual (e.g., average, etc.) density of any given injection or delivery of the fluid. In some non-limiting embodiments or aspects, central repository system 102 may determine the statistical parameter for a density of the plurality of different fluids.

As shown in FIG. 3, at step 308, process 300 determines whether a density of a fluid and/or a statistical parameter of the density of the fluid are within one or more threshold values. For example, central repository system 102 may determine whether the density of the fluid and/or the statistical parameter of the density of the fluid are within one or more threshold values (e.g., within 0.1% to 1%, 1% to 5%, 5% to 10% and/or the like). As an example, central repository system 102 may determine at least one of (i) whether the determined density is within a threshold value of the previously determined statistical parameter and (ii) whether the statistical parameter is within a threshold value of the previously determined statistical parameter, and flag the determined density for review in response to the determined density being determined to be outside the threshold value of the previously determined statistical parameter or the statistical parameter being determined to be outside the threshold value of the previously determined statistical parameter. For example, central repository system 102 may determine whether the determined density is within a threshold standard deviation (e.g., plus or minus 2 standard deviations, etc.) of a mean of the density of the fluid. As an example, central repository system 102 may determine whether the mean has shifted by more than a threshold percentage (e.g., 2%, etc.) and/or a standard deviation of the density of the fluid has shifted by more than a threshold percentage (e.g., 5%, etc.) as a result of the determined density of the fluid. In such an example, central repository system 102 may implement the determined density (e.g., update the previously determined statistical parameter, etc.) if the mean or the standard deviation is within 3% of the previous mean or standard deviation, flag the determined density for review if the mean or standard deviation is within 3% to 5% of the previous mean or standard deviation, and reject the determined density (e.g., not update the previously determined statistical parameter, etc.) if the mean or standard deviation value changes by more than 5% above or below the previous mean or standard deviation. Central repository system 102 may record results of this selection in terms of how often each option is selected and what the change represents and self-adjust boundaries or thresholds based on experience. Accordingly, if central repository system 102 determines that the determined density is within the threshold value of the previously determined statistical parameter and/or that the statistical parameter is within a threshold value(s) of the previously determined statistical parameter, processing may proceed to step 310. Flagging an item for review may include storing, in a data storage device, a review indicator for the item. The review indicator may be associated with a fluid, a density measurement for a portion of the fluid, or a statistical parameter for the fluid. The system may monitor the data storage device for review indicators and, upon detection of a review indicator, cause presentation of a perceivable message regarding the need for review of the item. The presentation may be provided using one or more of audio, visual (e.g., via graphical user interface), haptic, or multimodal devices.

The review process may be dynamically adjusted based on additional information received by the system. For example, if a manufacturer changes a preservative or alters pH balancing methods used for a drug, such changes may be referred to as a reformulation. Reformulations should be published through the Food and Drug Administration (FDA) and may also be published through a clearinghouse such as United States Pharmacopeia (USP). In such examples, the system may obtain periodic messages including reformulation information. Before flagging an item for review, an identifier for the fluid may be compared with the reformulation information to determine whether an adjustment was made by the manufacturer. If an adjustment is identified the flagging process may be omitted or the item may be flagged with a different status indicating that the item may not be due to systemic error but rather manufacturing changes. In some implementations, the adjustment may be time dependent and only affect the flagging if occurring within a period of time (e.g., within a month of receipt) of the item being flagged.

The time dependency may additionally or alternatively account for a transition period while sites may be concurrently using an "old" formulation and a "new" formulation. During such transition periods, the assessment may identify which sites that are using old stock, new stock, or a mix of old and new stock. Values reporting during the transition period may be filtered or otherwise held for review. The filtering may be applied for sites that appear to be reporting based on old stock until such time the site begins reporting values that more closely align with the new formulation. In some instances, it may be desirable to notify sites that an old formulation is still in use if such use occurs outside the transition period. This may help sites identify old or expired medications.

The notification of formulation changes may occur with or without notice. Manufacturers are supposed to change the unique identifier (e.g., NDC) for the mendicant when there is a significant formulation change. In general, changes in formulation might make a change of 1-2% in the density of an injection. To be meaningful in a system where minor variation (e.g., ±5%, ±2-5%, or ±5-10%) is permissible, changes have to exceed the upper limits of variation to achieve practical significance. One example of practical significance is where the variation produces a change to a computed volume that would be measurable with the tools at hand, such as in syringes. With a large enough data set, even relatively meaningless changes in the data can develop statistical significance. New formulations likely do not move instantaneously through the supply chain; rather they flow somewhat geographically, but also to larger facilities (e.g., hospitals) before hitting smaller facilities (e.g., hospitals). The system may include features to detect patterns in the data that suggest "pockets" of sites within which the density of a reformulated fluid has changed. The detection can be augmented by the introduction of a new NDC or set of NDC's, when notice is provided and available. Over time, the predominant form of any given reformulated injection will migrate to the newly reformulated product as the supply chain is depleted of old inventory.

In case that formulation changes are announced, the system may provide a review indicator (e.g., via a GUI) to identify that a particular injection, or family of injectable products has been reformulated, and to log the NDC's associated with that family of reformulated products. The system may additionally or alternatively begin segmenting out subsets of data that compare the mean density from the overall system, to the mean densities associated with the use of those particular NDC's. As time progresses and additional measurements are received, the system may detect a trend for the mean density among the reformulated product in comparison to the mean density for that medication in general. If the variance in density is less than the variation threshold (e.g., 5%) the system may ignore the measurement (e.g., filter it from consideration and/or inclusion in the data set). If the measurement exceeds the variation threshold, the value may be statistically blended to allow the aggregated measurement to drift toward the "new normal" that is the newly reformulated product.

As shown in FIG. 3, at step 310, process 300 includes providing a statistical parameter of a density of a fluid to a gravimetric verification system for updating a density value used in the gravimetric verification system for gravimetric verification. For example, central repository system 102 may provide the statistical parameter of the density of the fluid to gravimetric verification system 106a for updating a density value used in the gravimetric verification system for gravimetric verification. As an example, gravimetric verification system 106a may determine a second intended volume of a second portion of the fluid (e.g., a fluid of the same type of fluid) to be delivered to a second medication container and a second mass of the second portion of the fluid delivered to the second medication container; determine a second density of the of the fluid based on the second intended volume of the fluid and the second mass of the fluid; and compare the second density of the fluid to the statistical parameter of the density of the fluid to confirm whether a correct amount of the fluid is delivered into the second container.

In some non-limiting embodiments or aspects, central repository system 102 may receive, from at least one second gravimetric verification system 106b, a second intended volume of a fluid to be delivered to a medication container and a second mass of the fluid delivered to the medication container; determine a second density of the fluid based on the second intended volume of the fluid and the second mass of the fluid; determine the statistical parameter of the density of the fluid based on the second determined density of the fluid and the previously determined statistical parameter of the density of the fluid; and provide the statistical parameter of the density of the fluid to the gravimetric verification system 106a for updating the density value used in the gravimetric verification system 106a for gravimetric verification. Accordingly, a statistical model of the density that can be used to determine a range of densities experienced in the field for any particular concentration of any particular drug may be generated and provided to the one or more gravimetric verification systems 106.

In some non-limiting embodiments or aspects, central repository system 102 may determine an amount of change in the statistical parameter of the density of the fluid over a period time. The system 102 may determine, based on the density of the fluid and an additional density value of the fluid, which gravimetric verification system is as associated with the change in the statistical parameter. The association may be identified by detecting a density value that does not correspond to the current density for the fluid generated by the central repository system 102 based on one or more previously density measurements received from one or more gravimetric verification systems. By associating a change with a specific gravimetric verification system, the central repository system 102 can transmit a message to the gravimetric verification system identifying the discrepancy observed. In some implementations, the central repository system 102 may maintain a count or other metric of variance and, for sources that are associated with a metric indicating a threshold level of unreliability, the measurements from the gravimetric verification system may be filtered from inclusion in the repository. In some implementations, the central repository system 102 may transmit or cause transmission of a control message to the gravimetric verification system to adjust one or more function of the gravimetric verification system. For example, the deviations may be due to a malfunction in the hardware taking the measurements. In such instances, it may be desirable to adjust the hardware to alert to a potential malfunction or prevent use of one or more features of the hardware until checked. The control message may cause the gravimetric verification system to adjust by, for example, locking functionality from use (e.g., disable or remove an option from a user interface), adjusting the power state (e.g., shut the system down), initiating an auto-calibration or self-check process at the system to correct or identify potential errors, causing recalibration of the gravimetric verification system, and/or changing the state of another physical element included in the gravimetric verification system and/or the IVWMS 100. In some implementations, the central repository system 102 may transmit or cause transmission of a control message to another component of the IVWMS 100, such as a labeling system. For example, the control message may cause the labeling system to adjust one or more of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof. This can help to prevent or limit the spread of a discrepancy or other error detected by the IVWMS 100.

Figure 4:
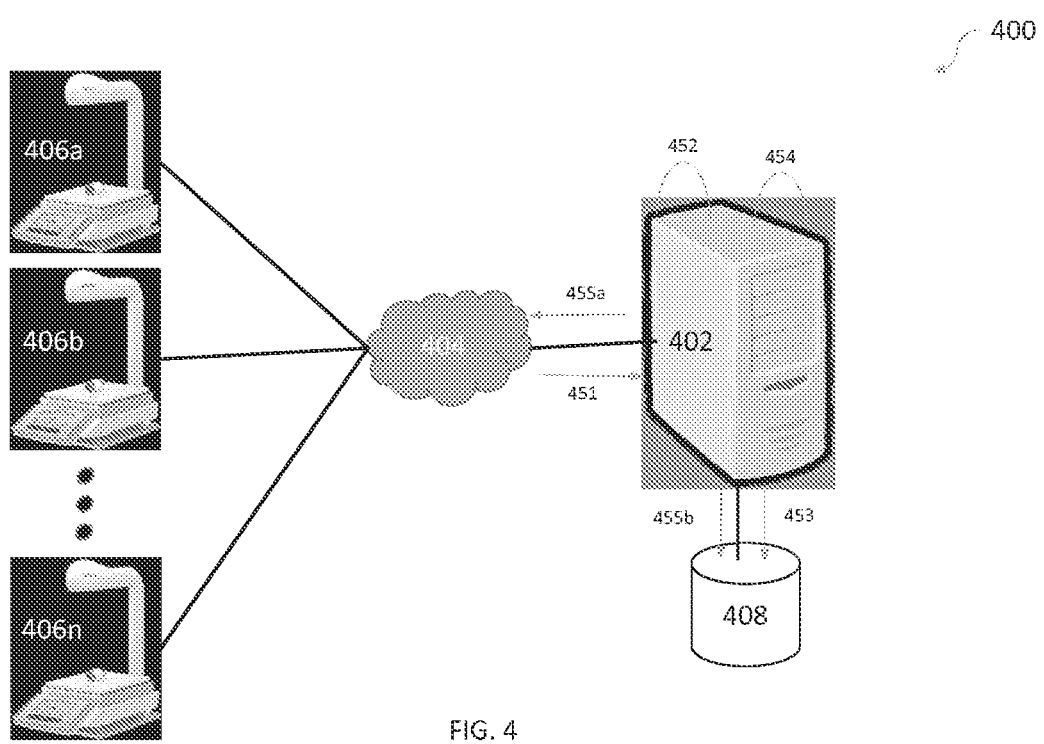
FIG. 4 is a schematic diagram of an IV workflow management system including an overview of a non-limiting embodiment or aspect of an implementation relating to a process for gravimetric verification using fluid volumetrics and density features described herein.

Referring now to FIG. 4. FIG. 4 is diagram of an overview of a non-limiting embodiment or aspect of an IVWMS 400 for performing a process for gravimetric verification using fluid volumetrics and density features described herein. The IVWMS 400 may include one or more of the same or similar components, properties, and/or features of the IVWMS 100. As shown in FIG. 4, the IVWMS 400 includes central repository system 402, communication network 404, gravimetric verification systems (or IV workflow systems) 406a, 406b, . . . 406n (e.g., where n is an integer larger than 2, etc.), and/or central repository data store 408. In some non-limiting embodiments or aspects, central repository system 402 can be the same or similar to central repository system 102. In some non-limiting embodiments or aspects, communication network 404 can be the same or similar to communication network 104. In some non-limiting embodiments or aspects, gravimetric verification systems (or IV workflow systems) 406a, 406b, . . . 406n can be the same or similar to gravimetric verification systems 106a, 106b, . . . 106n. In some non-limiting embodiments or aspects, central repository system 402 may be directly coupled or indirectly coupled (e.g., via communication network 404) with central repository data store 408.

The IVWMS 400 relating to a process for gravimetric verification using fluid volumetrics and density features shown in FIG. 4 may generate a new expected density for a fluid in consideration of new measurements. If the new value is unlikely to be sufficiently accurate for inclusion in a new computation of a mean density for the specified fluid (e.g., fails to satisfy a threshold difference between the new value and a mean value, etc.), one or more of central repository system 402, one or more of the gravimetric verification systems (or IV workflow systems) 406a, 406b, . . . 406n, and/or central repository data store 408 can store or park the new value for review. If the new value is likely to be sufficiently accurate for inclusion in a new computation of a mean density for the specified fluid (e.g., satisfies a threshold difference between the new value and a mean value, etc.), the new value may be published as the new expected value for all instances of the fluid.

Referring to FIG. 4, via message 451, the central repository system 402 receives measurements for a portion of the fluid from, for example, the gravimetric verification system 406a. Via message 452, the central repository system 402 generates a density for the portion of the fluid based on the measurements received. Via message 453, the central repository system 402 adds the expected density to a set of densities for the fluid that were previously generated. Via message 454, the central repository system 402 generates a new expected density for the fluid and likelihood of new expected density for the fluid. The new expected density may be generated based on the prior and newly generated density for the fluid. This provides a sample set for assessing a density for the fluid globally rather than for a specific portion or instance. If the likelihood that the new expected density corresponds to a minimum likelihood threshold, the new density may be determined to be accurate. In such instances that the new density is determined to be accurate, via message (455a), the new density may be transmitted to the gravimetric verification systems 406a-n. The systems 406a-n may store the new density as a reference density for future gravimetric verification of other portions (e.g., other doses) of the fluid. If the likelihood that the new expected density does not correspond to the minimum likelihood threshold, via message (455b), the central repository system 402 may flag the new density and/or measurements for review. The flagging may include entering or altering a record in the central repository data store 408. In some implementations, additional control messages may be provided by the central repository system 402 such as a control message to cause an adjustment of a gravimetric verification system 406a-n, a labeling system, and/or the like, as described herein. The adjustment may include an adjustment to at least one of: a display, a power state of the gravimetric verification system, an operational status of the gravimetric verification system, or a configuration value used by the gravimetric verification system. In some implementations, if the new density does not correspond to the desired accuracy, the value may be filtered from further use as outlier. It may be desirable to also identify the source of the measurements for the inaccurate information and adjust how new measurements from the source are treated. For example, it may be that the source is misconfigured or miscalibrated. In such instances, central repository system 402 may filter any measurements for processing to avoid tainting the sample of densities. The correspondence or messages referenced at 455a or 455b may have more gradients whereby some relationship to the threshold or other measure of statistical significance of either the density value or likelihood are used to assess and/or select different actions.

Figure 5:
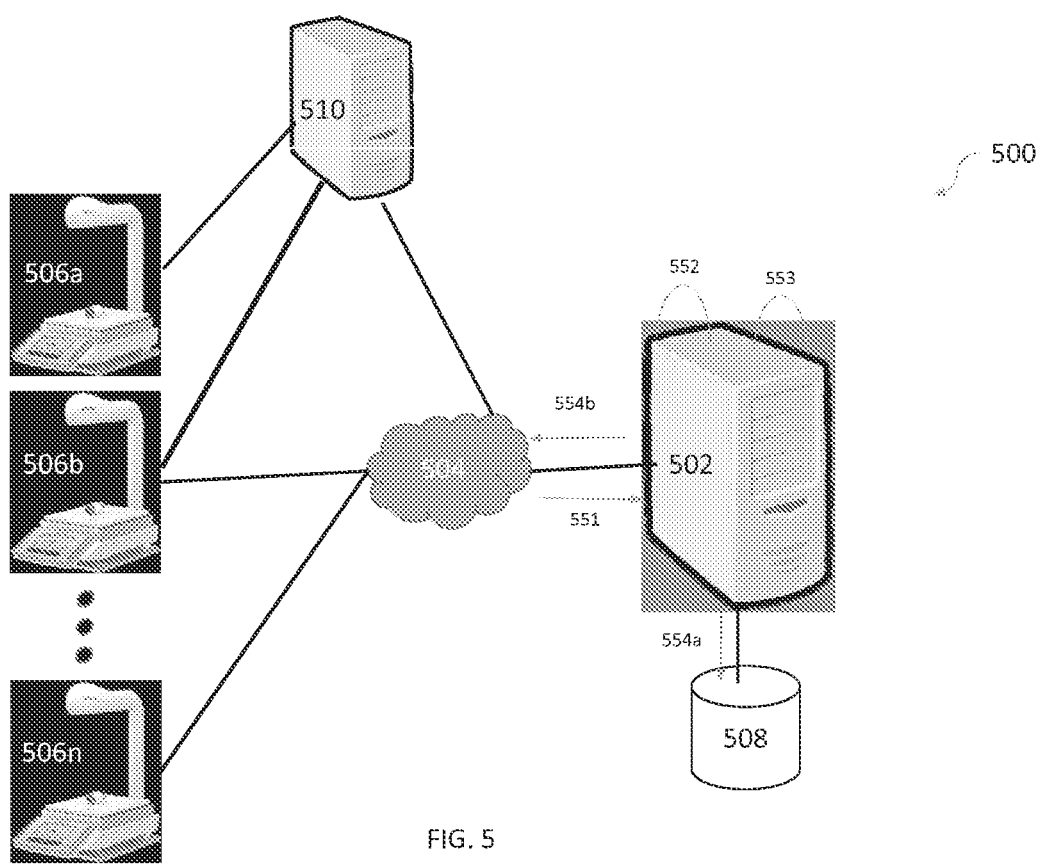
FIG. 5 is a schematic diagram of an IV workflow management system including an overview of a non-limiting embodiment or aspect of an implementation relating to a process for gravimetric verification using fluid volumetrics and density features described herein.

Referring now to FIG. 5. FIG. 5 is diagram of an overview of a non-limiting embodiment or aspect of an IVWMS 500 relating to a process for gravimetric verification using fluid volumetrics and density features described herein. The IVWMS 400 may include one or more of the same or similar components, properties, and/or features of the IVWMS 100, 400. As shown in FIG. 5, the IVWMS 500 includes central repository system 502, communication network 504, gravimetric verification systems (or IV workflow systems) 506a, 506b, . . . 506n (e.g., where n is an integer larger than 2, etc.), central repository data store 508, and/or IV workflow coordination server 510. In some non-limiting embodiments or aspects, central repository system 502 can be the same or similar to central repository system 102, 402. In some non-limiting embodiments or aspects, communication network 504 can be the same or similar to communication network 104, 404. In some non-limiting embodiments or aspects, gravimetric verification systems (or IV workflow systems) 506a, 506b, . . . 506n can be the same or similar to gravimetric verification systems 106a, 106b, . . . 106n, 406a, 406b, . . . 406n. In some non-limiting embodiments or aspects, central repository data store 508 can be the same or similar to central repository data store 408. In some non-limiting embodiments or aspects, central repository system 502 may be directly coupled or indirectly coupled (e.g., via communication network 504) with central repository data store 508. IV workflow coordination server 510 may be included to provide control and oversight of one or more of the gravimetric verification systems 506a-n. The IVWMS 500 for performing a process for gravimetric verification using fluid volumetrics and density features shown in FIG. 5 may be used to verify the quality of a measurement source to determine whether or not to include measurements in the crowdsourced corpus.

Referring to FIG. 5, via message 551, the central repository system 502 receives measurements for a portion of the fluid from, for example, the gravimetric verification system 506a. Via message 552, the central repository system 502 generates a density for the portion of the fluid based on the measurements. Via message 553, the central repository system 502 generates a new expected density for fluid and likelihood of new expected density for the fluid. Via message 554a, if the density for the portion of the fluid corresponds to current expected density (e.g., statistical mean of prior densities for portions of the fluid), the central repository system 502 may add measurements from source to data set associated with the fluid. In some implementations, the generated density may be added to the data set in place of or in conjunction with the measurements. If density for portion of the fluid does not correspond to the current expected density, via message 554b, the central repository system 502 may take further action (e.g., flag for review at the central repository system 502, flag for review at gravimetric verification system or workflow server, refuse receipt of further measurements from source gravimetric verification system, transmit alert to gravimetric verification system or coordination server, transmit control signal to adjust gravimetric verification system, etc.). The correspondence reference at 554a) or 554b may have more gradients whereby some relationship to the threshold or other measure of statistical significance of either the density value or likelihood are used to assess/selection different actions.

Figure 6:
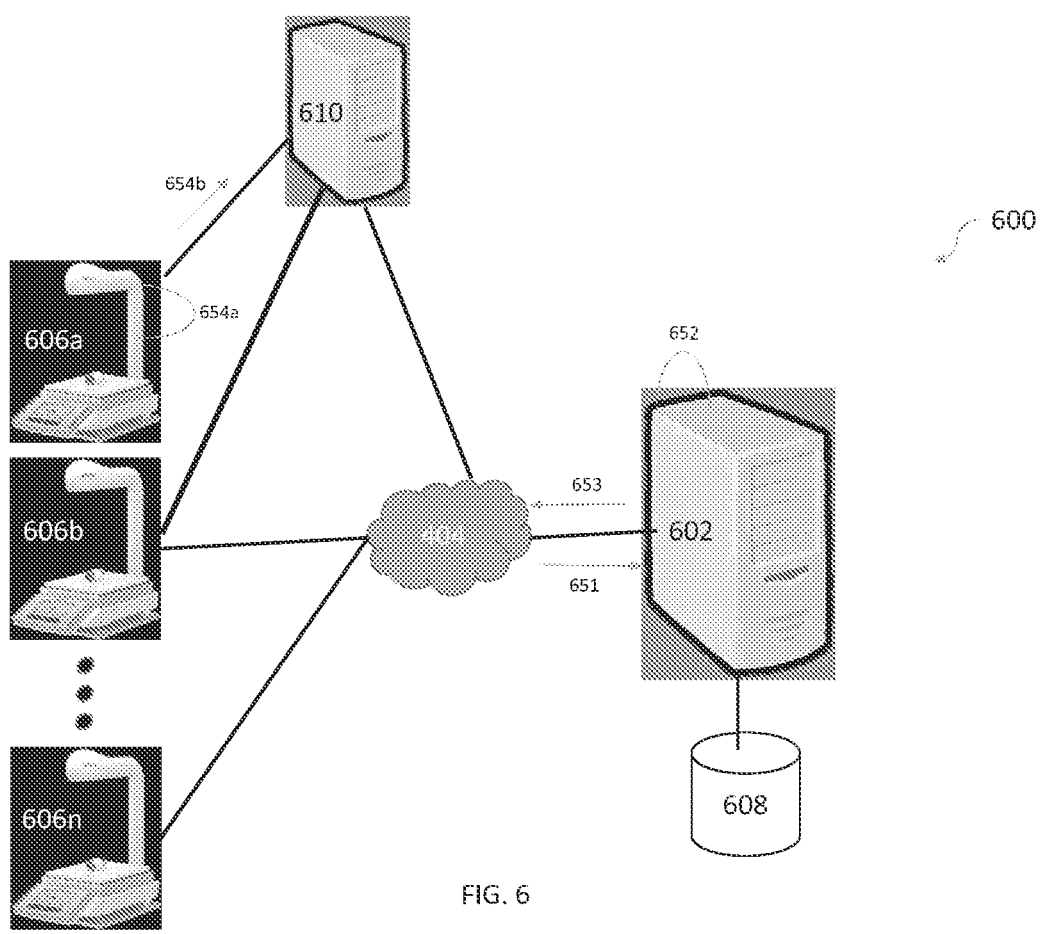
FIG. 6 is a schematic diagram of an IV workflow management system including an overview of a non-limiting embodiment or aspect of an implementation relating to a process for gravimetric verification using fluid volumetrics and density features described herein.

Referring now to FIG. 6, FIG. 6 is diagram of an overview of a non-limiting embodiment or aspect of an IVWMS 600 relating to a process for gravimetric verification using fluid volumetrics and density features described herein. The IVWMS 400 may include one or more of the same or similar components, properties, and/or features of the IVWMS 100, 400, 500. As shown in FIG. 6, IVWMS 600 includes central repository system 602, communication network 604, gravimetric verification systems (or IV workflow systems) 606a, 606b, . . . 606n (e.g., where n is an integer larger than 2, etc.), central repository data store 608, and/or IV workflow coordination server 610. In some non-limiting embodiments or aspects, central repository system 602 can be the same or similar central repository system 102, 402, 502. In some non-limiting embodiments or aspects, communication network 604 can be the same or similar to communication network 104, 404, 504. In some non-limiting embodiments or aspects, gravimetric verification systems (or IV workflow systems) 606a, 606b, ... 606n can be the same or similar to gravimetric verification systems 106a, 106b, ... 106n, 406a, 406b, ... 406n, 506a, 506b, ... 506n. In some non-limiting embodiments or aspects, central repository data store 608 can be the same or similar to central repository data store 408 and/or 508. In some non-limiting embodiments or aspects. IV workflow coordination server 610 can be the same or similar to IV workflow coordination server 510.

The IVWMS 600 for performing a process for gravimetric verification using fluid volumetrics and density features shown in FIG. 6 may offload the density calculation from the gravimetric verification system to a remote device (e.g., to central repository system 602, etc.). Central repository system 602 may convert the measurements to a density and compare the density with a crowdsourced expected density.

Referring to FIG. 6, via message 651, the central repository system 602 receives measurements for a portion of the fluid from, for example, gravimetric verification system 606a. Via message 652, the central repository system 602 generates (a) expected density for the portion of the fluid and (b) a likelihood of the expected density based on the pool of previous densities. Via message 653, the central repository system 602 transmits expected density and likelihood to the gravimetric verification system 606a. At gravimetric verification system 606a, if the likelihood corresponds to a minimum threshold, via message 654a, the gravimetric verification system 606a may use the expected density for verification of the fluid portion. However, if the likelihood does not correspond to a minimum threshold, via message 654b, the gravimetric verification system 606a may flag the portion for review or take other action to correct potential inaccuracy (e.g., recalibrate, disable a function, provide an alert message, etc.). The correspondence referenced at 654a or 654b may have more gradients whereby some relationship to the threshold or other measure of statistical significance of either the density value or likelihood are used to assess/selection different actions. The expected density may be used by the gravimetric verification system in to confirm a locally generated density, confirm measurements that were taken for a fluid portion, or other corrective/oversight action.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, web services, or rich site summary (RSS). In some implementations, a UI may be included in a stand-alone client (for example, thick client, fat client) configured to communicate (e.g., send or receive data) in accordance with one or more of the aspects described. The communication may be to or from a medical device, diagnostic device, monitoring device, or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, or the like. A message may, in some implementations, include a signal utilized to transmit one or more representations of the information. While recited in the singular, it will be understood that a message may be composed, transmitted, stored, received, etc. in multiple parts.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

Although embodiments or aspects have been described in detail for the purpose of illustration and description, it is to be understood that such detail is solely for that purpose and that embodiments or aspects are not limited to the disclosed embodiments or aspects, but, on the contrary, are intended to cover modifications and equivalent arrangements that are within the spirit and scope of the appended claims. For example, it is to be understood that the present disclosure contemplates that, to the extent possible, one or more features of any embodiment or aspect can be combined with one or more features of any other embodiment or aspect. In fact, any of these features can be combined in ways not specifically recited in the claims and/or disclosed in the specification. Although each dependent claim listed below may directly depend on only one claim, the disclosure of possible implementations includes each dependent claim in combination with every other claim in the claim set.

What is claimed is:

1. A system comprising:
a central repository system including one or more processors programmed and/or configured to:
receive, from a first gravimetric verification system, an identifier for a fluid, an intended volume of a first portion of the fluid to be delivered to a medication container, and a mass of the first portion of the fluid delivered to the medication container;

determine an expected density of the first portion of the fluid based on the intended volume of the first portion of the fluid and the mass of the first portion of the fluid;

determine a statistical parameter of a density of the fluid based at least in part on a relationship between the expected density and a set of densities of a plurality of portions of the fluid from additional gravimetric verification systems;

based at least in part on the statistical parameter, provide the expected density of the fluid to the first gravimetric verification system; and determine whether the statistical parameter corresponds to a threshold range or value compared to a previously determined statistical parameter to warrant at least one of: a modification to the existing density value or a publication of the expected density to the additional gravimetric verification systems.

2. The system of claim 1, wherein the one or more processors are further programmed and/or configured to:
receive, from a second gravimetric verification system, a second intended volume of a second portion of the fluid to be delivered to a second medication container and a second mass of the second portion of the fluid delivered to the second medication container;
determine a second density of the fluid based on the second intended volume and the second mass;
determine the statistical parameter of the density of the fluid based at least in part on a relationship between the second density and the set of densities of the plurality of portions of the fluid from the additional gravimetric verification systems, wherein the set of densities includes the expected density for the first portion of the fluid; and
based at least in part on the statistical parameter, provide the second density of the fluid to the first gravimetric verification system for updating a density value used by the first gravimetric verification system for gravimetric verification of the fluid.

3. The system of claim 2, wherein the one or more processors are further programmed and/or configured to:
determine an amount of change in the statistical parameter of the density of the fluid over a period time; and
determine, based on the determined density of the fluid and the second determined density of the of the fluid, at least one of the first gravimetric verification system and the second gravimetric verification system as associated with the change in the statistical parameter.

4. The system of claim 3, wherein the one or more processors are further programmed and/or configured to:
receive a measurement from the first gravimetric verification system associated with the change in the statistical parameter; and
transmit a message indicating refusal of the measurement.

5. The system of claim 3, wherein the one or more processors are further programmed and/or configured to:
transmit a control message to cause an adjustment of the first gravimetric verification system associated with the change in the statistical parameter, wherein the adjustment comprises an adjustment to at least one of: a display, a power state of the first gravimetric verification system associated with the change in the statistical parameter, an operational status of the first gravimetric verification system associated with the change in the statistical parameter, a configuration value used by the first gravimetric verification system associated with the change in the statistical parameter, or any combination thereof.

6. The system of claim 1, further comprising:
the first gravimetric verification system, wherein the first gravimetric verification system includes one or more processors programmed and/or configured to:
determine a second intended volume of a portion of the fluid to be delivered to a second medication container and a second mass of the portion of the fluid delivered to the second medication container;
determine a second density of the of the fluid based on the second intended volume and the second mass; and
determine that the second density corresponds to the statistical parameter of the expected density of the fluid; and
adjust at least one element of the first gravimetric verification system, wherein the adjustment includes at least one of: authorizing dispensing of the second medical container or printing a label for the second medical container wherein the label includes at least one of (i) the second density information, (ii) the second intended volume; (iii) the second mass, (iv) an identifier for the fluid; (v) an identifier for the portion of the fluid, or any combination thereof.

7. The system of claim 1, wherein the statistical parameter includes a mean of a plurality of densities for portions of the fluid, wherein the plurality of densities includes the expected density of the first portion of the fluid.

8. The system of claim 7, wherein the one or more processors are further programmed and/or configured to:
obtain, from a memory accessible by the central repository system, historical means for the fluid including a first mean value for a first point in time before receipt of the intended volume of the first portion and a second mean value for a second point in time before the first point in time;
detect a density drift over time based on the historical means and the mean, wherein the drift indicates a statistically significant change over a time period spanning from the second point in time to the time the intended volume of the first portion was received; and
transmit a message indicating a change to the density for the fluid to the additional gravimetric verification systems for use in verifying other portions of the fluid.

9. The system of claim 1, wherein the statistical parameter includes a deviation of the expected density from a mean of a plurality of densities for portions of the fluid.

10. The system of claim 1, wherein the statistical parameter includes a density likelihood indicating a degree of correspondence between the expected density for the first portion of the fluid and an aggregated density for previously generated densities for other portions of the fluid.

11. The system of claim 10, wherein the one or more processors are further programmed and/or configured to:
route the expected density to a processing path of a plurality of processing paths, the routing based on the degree of correspondence, wherein the plurality of processing paths includes:
for a first degree of correspondence, generating a mean statistical density for the fluid including the expected density for the first portion of the fluid;
for a second degree of correspondence, filtering the expected density from consideration for the fluid; and for a third degree of correspondence, transmitting the expected density for presentation and review via a graphical user interface.

12. The system of claim 1, wherein the one or more processors are further programmed and/or configured to:
obtain, from a memory accessible by the central repository system, an accuracy threshold for the fluid; and
determine that the statistical parameter corresponds to the accuracy threshold.

13. The system of claim 1, wherein the medication container is not a syringe.

14. A computer-implemented method comprising:
receiving, with at least one processor, from a first gravimetric verification system, an identifier for a fluid, an intended volume of a first portion of the fluid to be delivered to a medication container, and a mass of the first portion of the fluid delivered to the medication container;
determining, with at least one processor, an expected density of the first portion of the fluid based on the intended volume of the first portion of the fluid and the mass of the first portion of the fluid;
determining, with at least one processor, a statistical parameter of a density of the fluid based at least in part on a relationship between the expected density and a set of densities of a plurality of portions of the fluid from additional gravimetric verification systems;
based at least in part on the statistical parameter, providing, with at least one processor, the expected density of the fluid to the first gravimetric verification system; and
determining, with at least one processor, whether the statistical parameter corresponds to a threshold range or value compared to a previously determined statistical parameter to warrant at least one of: a modification to the existing density value or a publication of the expected density to the plurality of gravimetric verification systems.

15. The computer-implemented method of claim 14, further comprising:
receiving, with at least one processor, from a second gravimetric verification system, a second intended volume of a second portion of the fluid to be delivered to a second medication container and a second mass of the second portion of the fluid delivered to the second medication container;
determining, with at least one processor, a second density of the fluid based on the second intended volume and the second mass;
determining, with at least one processor, the statistical parameter of the density of the fluid based at least in part on a relationship between the second density and the set of densities of the plurality of portions of the fluid from the additional gravimetric verification systems, wherein the set of densities includes the expected density for the first portion of the fluid; and
based at least in part on the statistical parameter, providing, with at least one processor, the second density of the fluid to the first gravimetric verification system for updating a density value used by the first gravimetric verification system for gravimetric verification of the fluid.

16. The computer-implemented method of claim 15, further comprising:
determining, with at least one processor, an amount of change in the statistical parameter of the density of the fluid over a period time; and
determining, with at least one processor, based on the determined density of the fluid and the second determined density of the of the fluid, at least one of the first gravimetric verification system and the second gravimetric verification system as associated with the change in the statistical parameter.

17. The computer-implemented method of claim 16, further comprising:
receiving, with at least one processor, a measurement from the first gravimetric verification system associated with the change in the statistical parameter; and
transmitting, with at least one processor, a message indicating refusal of the measurement.

18. A computer program product comprising at least one non-transitory computer-readable medium including program instructions that, when executed by at least one processor, cause the at least one processor to:
receive, from a first gravimetric verification system, an identifier for a fluid, an intended volume of a first portion of the fluid to be delivered to a medication container, and a mass of the first portion of the fluid delivered to the medication container;
determine an expected density of the first portion of the fluid based on the intended volume of the first portion of the fluid and the mass of the first portion of the fluid;
determine a statistical parameter of a density of the fluid based at least in part on a relationship between the expected density and a set of densities of a plurality of portions of the fluid from additional gravimetric verification systems;
based at least in part on the statistical parameter, provide the expected density of the fluid to the first gravimetric verification system; and
determine whether the statistical parameter corresponds to a threshold range or value compared to a previously determined statistical parameter to warrant at least one of: a modification to the existing density value or a publication of the expected density to the plurality of additional gravimetric verification systems.

* * * * *